(12) United States Patent
Neeper et al.

(10) Patent No.: US 7,635,246 B2
(45) Date of Patent: Dec. 22, 2009

(54) DEVICE AND METHOD FOR RETRIEVING OR REPLACING A TRAY WITHIN A STORAGE COMPARTMENT

(75) Inventors: Robert K. Neeper, Ramona, CA (US); Rhett L Affleck, Poway, CA (US); John E. Lillig, Ramona, CA (US)

(73) Assignee: Nexus Biosystems, Inc., Poway, CA (US)

( * ) Notice: Subject to any disclaimer, the term of this patent is extended or adjusted under 35 U.S.C. 154(b) by 4 days.

(21) Appl. No.: 11/925,912

(22) Filed: Oct. 27, 2007

(65) Prior Publication Data

US 2008/0044261 A1 Feb. 21, 2008

Related U.S. Application Data

(63) Continuation of application No. 11/626,359, filed on Jan. 23, 2007.

(60) Provisional application No. 60/761,736, filed on Jan. 23, 2006, provisional application No. 60/799,706, filed on May 11, 2006, provisional application No. 60/808,470, filed on May 24, 2006, provisional application No. 60/820,338, filed on Jul. 25, 2006.

(51) Int. Cl.
*B65G 1/00* (2006.01)
*B65G 65/00* (2006.01)

(52) U.S. Cl. .............. 414/280; 414/331.02; 414/331.08

(58) Field of Classification Search ................. 414/280, 414/331.02, 331.08
See application file for complete search history.

(56) References Cited

U.S. PATENT DOCUMENTS 2,074,974 A 3/1937 Stewart (Continued)

FOREIGN PATENT DOCUMENTS

DE 19716913 A1 11/1998

(Continued)

OTHER PUBLICATIONS

Yates. "Compound Management Comes of Age," Drug Discovery World, 2003, pp. 35-42.

(Continued)

*Primary Examiner*—Saúl J Rodríguez
*Assistant Examiner*—Jonathan D Snelting
(74) *Attorney, Agent, or Firm*—Procopio, Cory, Hargreaves & Savitch, LLP; Eleanor M. Musick

(57) ABSTRACT

An automated storage system for storing large quantities of samples in trays includes a storage compartment, a tray shuttle compartment abutting the storage compartment on one side and a plurality of independent modules on the other side. The modules perform processing of samples that are retrieved from the storage compartment by a tray shuttle, including extraction of selected samples from retrieved source trays and transfer of the selected samples into a separate, destination tray that can be further processed or removed from the system for use. The independent operation of the modules permits handling and processing to be performed simultaneously by different modules while the tray shuttle accesses additional samples within the storage compartment. In one embodiment, a vertical carousel is used to vertically align a desired tray with the tray shuttle, while the tray shuttle operates within a horizontal plane.

11 Claims, 28 Drawing Sheets

U.S. PATENT DOCUMENTS

| | | | |
|---|---|---|---|
| 3,753,657 A | | 8/1973 | Downing et al. |
| 3,883,008 A | * | 5/1975 | Castaldi, John A. ......... 414/270 |
| 4,004,883 A | | 1/1977 | Meyer et al. |
| 4,199,013 A | | 4/1980 | Reich et al. |
| 4,422,151 A | | 12/1983 | Gilson |
| 4,480,738 A | | 11/1984 | Mattson |
| 4,483,927 A | | 11/1984 | Takekawa |
| 4,609,017 A | | 9/1986 | Coulter et al. |
| 4,928,502 A | | 5/1990 | Kumada et al. |
| 5,055,408 A | | 10/1991 | Higo et al. |
| 5,063,068 A | | 11/1991 | Cavanagh |
| 5,122,342 A | | 6/1992 | McCulloch et al. |
| 5,161,929 A | | 11/1992 | Lichti |
| 5,286,652 A | | 2/1994 | James et al. |
| 5,499,707 A | * | 3/1996 | Steury ........................ 194/217 |
| 5,544,996 A | | 8/1996 | Castaldi et al. |
| 5,593,267 A | | 1/1997 | McDonald et al. |
| 5,795,547 A | | 8/1998 | Moser et al. |
| 5,921,739 A | | 7/1999 | Keip |
| 6,068,437 A | * | 5/2000 | Boje et al. ............. 414/331.02 |
| 6,113,336 A | | 9/2000 | Chang et al. |
| 6,148,878 A | | 11/2000 | Ganz et al. |
| 6,267,927 B1 | | 7/2001 | Longedo et al. |
| 6,325,114 B1 | | 12/2001 | Bevirt et al. |
| 6,360,792 B1 | | 3/2002 | Ganz et al. |
| 6,467,285 B2 | | 10/2002 | Felder et al. |
| 6,489,169 B1 | | 12/2002 | Cohen et al. |
| 6,543,203 B2 | | 4/2003 | Thompson et al. |
| 6,551,833 B1 | | 4/2003 | Lehtinen et al. |
| 6,637,473 B2 | | 10/2003 | Ganz et al. |
| 6,663,334 B2 | | 12/2003 | Warhurst et al. |
| 6,694,767 B2 | | 2/2004 | Junca et al. |
| 6,715,910 B2 | | 4/2004 | Robey |
| 6,827,907 B2 | | 12/2004 | Fattinger et al. |
| 6,890,485 B1 | | 5/2005 | Stylli et al. |
| 6,896,848 B1 | | 5/2005 | Warhurst et al. |
| 6,908,737 B2 | | 6/2005 | Ravkin et al. |
| 6,936,167 B2 | | 8/2005 | Hobbs et al. |
| 6,985,616 B2 | | 1/2006 | Ganz et al. |
| 2002/0098598 A1 | | 7/2002 | Coffen et al. |
| 2002/0102149 A1 | | 8/2002 | Warhurst et al. |
| 2003/0059287 A1 | | 3/2003 | Warhurst et al. |
| 2003/0059764 A1 | | 3/2003 | Ravkin et al. |
| 2003/0106492 A1 | | 6/2003 | Levinson et al. |
| 2003/0129654 A1 | | 7/2003 | Ravkin et al. |
| 2003/0185657 A1 | | 10/2003 | Stefani |
| 2003/0202905 A1 | | 10/2003 | Devlin et al. |
| 2003/0209091 A1 | | 11/2003 | Fattinger et al. |
| 2004/0096302 A1 | * | 5/2004 | Bouche et al. ............... 414/280 |
| 2004/0208792 A1 | | 10/2004 | Linton et al. |
| 2005/0009113 A1 | | 1/2005 | Goldbard et al. |
| 2005/0026295 A1 | | 2/2005 | Harding et al. |
| 2005/0092643 A1 | | 5/2005 | Craven |
| 2005/0250210 A1 | | 11/2005 | Pilkington et al. |
| 2006/0045674 A1 | | 3/2006 | Craven |
| 2006/0053825 A1 | | 3/2006 | Owen et al. |

FOREIGN PATENT DOCUMENTS

| | | |
|---|---|---|
| DE | 10157121 A1 | 5/2003 |
| FR | 2811414 A1 | 1/2002 |
| JP | 10024911 | 1/1998 |
| WO | 97/31609 | 9/1997 |
| WO | WO01/54817 | 8/2001 |
| ZA | 9803445 A | 11/1998 |

OTHER PUBLICATIONS

PCT/US07/60936, International Search Report and Written Opinion, May 2, 2008.

* cited by examiner

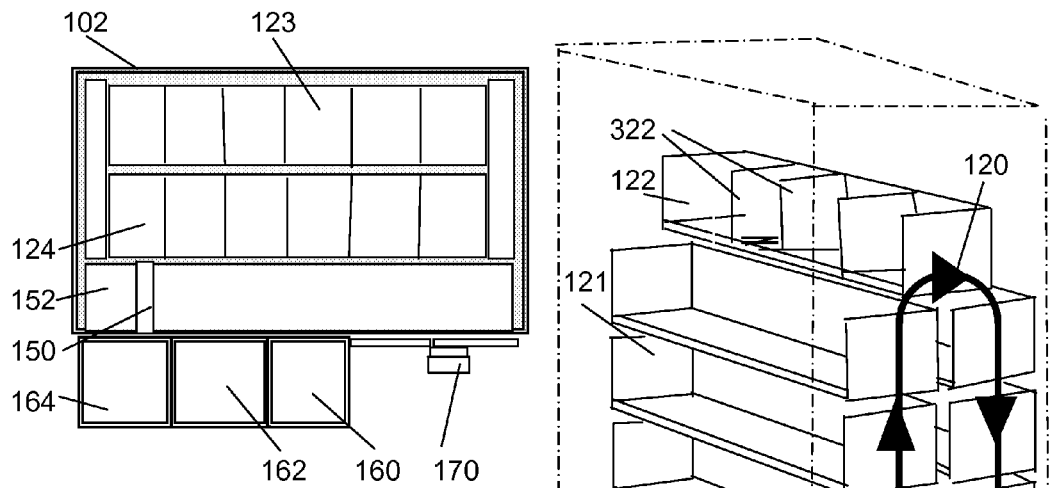
FIG. 2
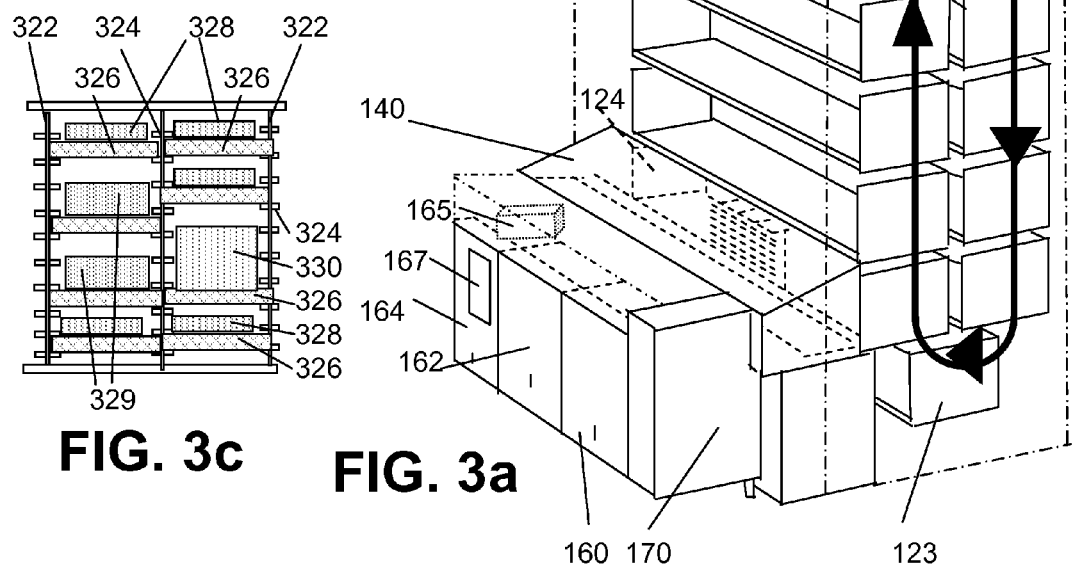
FIG. 3c  FIG. 3a

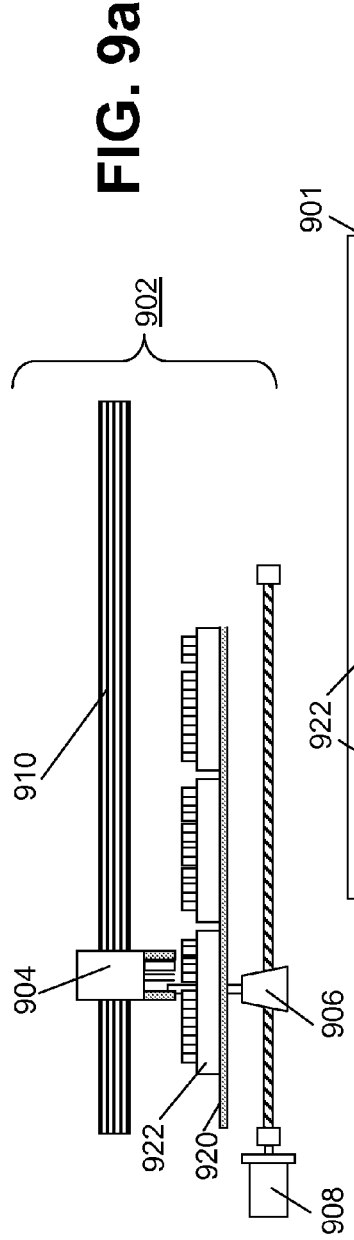

DEVICE AND METHOD FOR RETRIEVING OR REPLACING A TRAY WITHIN A STORAGE COMPARTMENT

RELATED APPLICATIONS

This application is a continuation of application Ser. No. 11/626,359, filed Jan. 23, 2007, which claims benefit of the priority of U.S. Provisional Applications No. 60/761,736, filed Jan. 23, 2006, No. 60/799,706, filed May 11, 2006, No. 60/808,470, filed May 24, 2006, and No. 60/820,338, filed Jul. 25, 2006, each of which is incorporated herein by reference in its entirety.

FIELD OF THE INVENTION

The present invention relates for systems for handling and storing biological or chemical samples, and more specifically to an automated system for storage, retrieval and management of large numbers of samples retained in sealed arrays of storage containers.

BACKGROUND OF THE INVENTION

Many scientific and medical organizations, including industrial concerns, regulatory agencies, research laboratories, and academic institutions, have the need for secure storage of very large numbers, e.g., a few thousand up to multiple millions, of samples and specimens. Such fields include pharmaceutical, biotechnology, laboratory diagnostics, genomics, biospecimen, forensic, agrichemical and specialty chemical. Depending on the application, the sample sizes can vary from tens of microliters to several drams, which are stored in small, sealed plastic tubes or vials. These containers are retained in a rack that allows individual samples to be inserted or removed without removing an entire rack, or the tray the holds one or more racks. To extend the useful lifetime of the samples, they are stored in a controlled environment of low temperature (typically −20° to −80° C. or lower), low humidity, and inert gas (nitrogen), and are subjected to as little environmental variation as possible. In order to handle very large numbers of samples in the most efficient manner, a number of considerations must be made to enhance the system's flexibility and adaptability for different applications with the smallest possible footprint to minimize the use of valuable laboratory space.

An overview of currently available compound storage systems and technologies is provided by Dr. John Comley in his article entitled "Compound Management in pursuit of sample integrity", published in *Drug Discovery World*, Spring 2005, pp. 59-78, which is incorporated herein by reference.

Tracking of the samples is essential, and the sample containers, racks and trays are usually labeled with a bar code or other machine-readable identifier. The identity and location of each sample is stored in a system memory that maintains records for all samples in the storage system so that individual samples or subsets of samples can be identified and rapidly retrieved from storage. Ideally, the retrieval process should occur without unnecessarily exposing samples to thawing or moisture, which means that the system must be capable of selecting individual samples from one or more racks in the storage compartment while minimizing exposure of other samples in the storage compartment, or in the same trays, to an environmental change. It is also important that the system be reliable so that it can be serviced without risking exposure of the samples to undesirable conditions.

To prevent evaporation of the sample or exposure to contaminants during storage, the containers are usually covered with a cap or membrane stretched across the open end of the container. In order to deal efficiently with the large numbers of containers in a tray, systems are commercially available to simultaneously seal all containers within the tray with a sheet of material, such as foil or laminated polymer, that is heat sealed or otherwise adhered to the top edges of all of the containers. These seals are pierceable or peelable to permit access to the sample. After the containers are sealed, the excess seal material between the containers is cut to separate the individual containers for subsequent retrieval without requiring the entire tray of containers to be thawed. After die cutting of the seals, the tray of containers is placed in storage. The die cutting operation requires a separate handling step, and usually, an additional piece of equipment with complex tooling that is specifically designed for a certain size and shape of tube, thus limiting the type of containers that can be used, or requiring that multiple die cutting tools be available.

In certain applications, the samples are preferably stored at ultra-low temperatures (−80° C. or lower), however, this cold environment can be hazardous to the electro-mechanical devices that are necessary for operation of an automated system. Lubricants are less effective at such low temperatures, making the robotics less reliable. Maintenance of robotics in the sample storage area is particularly a problem because the storage environment must be thawed and opened, subjecting the samples to condensation and possible thawing. Some commercial systems isolate the robotics in a somewhat warmer compartment (−20° C.), passing the samples between the two compartments. In such systems, an insulating wall must be created between the two compartments to maintain the temperatures in each compartment.

In existing systems, the sample storage areas have removable doors that are opened to obtain access to the trays. In others, the trays (or stacks of trays), have a block of insulating material at one end so that all trays together combine to form an insulated wall. When a tray is removed, the insulating material associated with that tray is also removed and must be replaced with a dummy block to maintain the integrity of the insulating wall. This replacement process takes time, however, increasing the risk of temperature change in one or both compartments.

In large storage applications, the samples may need to be accessed by multiple groups whose laboratory areas are in different locations within a facility, possibly even on different floors of a multi-story building. Access for loading and unloading sample containers in existing compound storage systems is located at a single location at the base of the storage unit. This often results in transporting large numbers of samples on carts and potentially exposing them to undesirable conditions. Further, with all groups needing to access their samples from a single station, time will be lost waiting for another user to finish their sample storage or retrieval operation.

The present invention is directed to storage systems that address the foregoing concerns to provide the flexibility and ease of use of large volume sample storage system.

BRIEF SUMMARY OF THE INVENTION

An automated storage system for storing large quantities of samples in trays includes a refrigerated storage compartment, a tray shuttle compartment abutting the storage compartment on one side and a plurality of independent modules on the other side. The modules perform processing of samples that are retrieved from the storage compartment by a tray shuttle, including extraction of selected samples from retrieved source trays and transfer of the selected samples into a separate, destination tray that can be further processed or removed from the system for use. The independent operation of the modules permits handling and processing to be performed simultaneously by different modules while the tray shuttle accesses additional samples within the storage compartment.

In a first exemplary embodiment, the automated sample storage and management system of the present invention employs a vertical storage carousel for the refrigerated storage compartment. Trays containing one or more arrays of individual, removable sample containers fit into a plurality of slots located in carriers that rotate around the carousel. The slots are configured to permit sufficient clearance between vertically adjacent trays to accept a variety of different size sample containers or well plates. The vertical carousel reduces the footprint of the system and greatly improves reliability since the carousel operation requires only a single motor that provides forward or reverse rotation to position the desired tray, or tray slot, in alignment with a horizontal tray loader/unloader mechanism, or "shuttle."

The vertical carousal storage mechanism combined with the horizontal tray shuttle allows retrieval times to be minimized by organizing the sequence of desired samples according to their locations in the carousel. As one sample is retrieved, the next one on the list can be pre-positioned for retrieval by rotating the carousel to move the next tray to the level of the tray shuttle. Other systems have fixed locations for the samples. They can retrieve trays quickly when the requested samples are located near each other, but become substantially slower when retrieving samples stored at the most distant locations of the storage area.

The vertical carousel minimizes the mechanics necessary to interface with the tray shuttle that moves trays between the storage compartment and one or more modules used for processing or inspection of the samples. Because the vertical carousal moves vertically, a single horizontal axis is capable of providing access to every carrier and tray on the carousel. The tray shuttle is a conveyor on the horizontal axis that is able to retrieve any tray across the entire width of the carousel. The only component of the tray shuttle that extends into the storage space is the tray hook. This rotating hook/lever device is able to pull or push a tray to insert it into or remove it from a slot on the carousel, to position the tray on the conveyor and to move it to any location where an operation is to be performed.

One or more modules are located on the front of the tray conveyor, on the opposite side from the storage compartment. Each module is capable of receiving one or more trays from the tray conveyor and performing some operation on the trays, such as modifying the contents of a particular tray, selecting, or "cherry picking", specific samples from a tray and placing them in another tray, defrosting a tray for use, removal of the samples for use, or inspection of the samples. The modules can be insulated and have a controlled atmosphere, including being cooled to the same temperature as the tray conveyor and/or filled with a gas to create an inert atmosphere. Because the tray conveyor and modules are external to the storage compartment, they can be removed or serviced without disrupting the frozen environment of the stored samples.

The modules may include liquid handling devices that can receive a defrosted tray, and at room temperature, preferably in an inert atmosphere, de-cap the containers, and aspirate and dispense a portion of the sample without removing the sample container from the system.

A significant benefit of the discrete modules is that it is practical to fill the storage compartment with an inert gas such as nitrogen, which reduces concerns about contamination due to water or oxygen. Since there is no need for human access to the storage area, the use of nitrogen does not present a health hazard to those using the system.

The modular design also allows the system to be accessed at different elevations along the height of the vertical carousel in addition to or other than the base of the system. This feature is useful where the storage compartment is tall enough to span multiple levels of a laboratory facility. The nature of the carousel allows sample carriers to be positioned at any level. By providing a tray shuttle, module(s) and system control station on a second, third, or other floor, different laboratories can have localized access to a common storage compartment. Software in the system controller will prioritize requests for access in situations where requests are submitted at or near the same time from different laboratories.

In occasions where space is available in a basement, but where access would be inconvenient or undesirable, the system can be configured to have access points only on the first and/or second floors with no access point in the basement. This can add considerable storage capacity without taking up valuable laboratory floor space.

Each of the modules is capable of independent operation, allowing multiple operations to be performed in parallel, and at least some of the modules include the ability to handle multiple trays at one time. This allows removal or replacement of trays in a module without the need to halt the operation of that module. For a selector, or "cherry-picking", module, this means that the mechanism can run continuously. Two source tray locations are provided so that while the mechanism is picking from one tray, the other can be replaced. The single destination tray is replaced as it is filled. This technique allows the picking rate to be considerably faster than existing methods because there is no down-time for the picking mechanism. The inventive design also improves reliability.

The selector module includes a pusher mechanism, which lifts the sample containers up and out of the tray, and a pick head, which has one or more cavities for receiving the containers that are lifted by the pusher mechanism. The pusher mechanism moves independently from the moveable pick head, allowing the pick head to receive multiple tubes from different locations of a tray. The pick head is then moved to a destination over destination tray and the ejector mechanism is actuated, placing all tubes in one motion.

The selector module can be configured to perform the function of die cutting, thus eliminating the need for an additional step, and additional instrumentation, for separating containers within a rack that have been sealed with a sheet of foil or polymer. In this embodiment, one or more cavities in the pick head have a sharp edge that is capable of cutting the seal around the perimeter of the sample container when it is pushed upward by the pusher mechanism. This allows the tubes to be stored with the seal intact until needed. Typically only a few samples are needed at a time, so the seal is cut only around the containers of the samples that are desired when they are prepared for selection.

In an alternate embodiment of the storage compartment that is particularly suitable for ultra cold storage, the vertical carousel is replaced by stationary racks and a gantry-type tray shuttle, capable of vertical and horizontal movement, which is housed within a warmer (~−20° C.) compartment. The storage compartment is separated from the tray shuttle/gantry compartment by stacks of foam bricks that are arranged to create a robotically friendly insulating wall in front of the storage trays. The blocks are arranged in stacks and held in place by gravity. Guide rails on either side of the stacks constrain the blocks against lateral movement while allowing them to slide up and down freely. To access a particular tray, the robotic loader/unloader moves to a block in front of the desired tray, extends a pin or plate into a corresponding recess in the block, then lifts all of the blocks above that point. The tray of interest is extracted and the blocks are lowered to the original position. The blocks can be of any size but it is preferable to keep them relatively small to minimize size of the gap needed to access the desired tray position and, thus, minimize any temperature change that might occur when the gap is temporarily opened in the wall. The inventive approach allows the opening to be immediately closed after the tray is extracted, without the delays experienced with prior art systems that require a substitute tray to be retrieved to plug the hole left by the extracted tray.

BRIEF DESCRIPTION OF THE DRAWINGS

The present invention will be more clearly understood from the following detailed description of the preferred embodiments of the invention and from the attached drawings, in which:

FIG. 2 is a diagrammatic cross-sectional view taken along line 2-2 of FIG. 1, showing the storage unit, tray shuttle mechanism, and exemplary external modules.

FIG. 3a is a diagrammatic perspective view of the first embodiment with the storage unit housing removed; FIG. 3c is a detail view of versatile tray slots that permit storage of different size sample containers.

FIGS. 9a and 9b are diagrammatic views (front and top) of the tube picking function.

DETAILED DESCRIPTION OF THE PREFERRED EMBODIMENTS

For purposes of the detailed description of the preferred embodiments, the following definitions are used:

A "sample" is used to describe a material (compound, biological specimen, or other substance) that is or can be stored in a storage system, as well as a tube, vial and similar container which is the lowest unit of storage for retaining the stored material.

An "array" includes plates and racks that organize samples in a fixed arrangements. Racks hold removable sample containers while plates have non-removable wells. Such racks are generally configured as an array of vertical, open ended sleeves or slots, permitting access to the removable containers retained within the slots.

A "tray" is a flat frame or container the holds multiple arrays. Generally, all trays within the storage system will be of the same length and width, and the arrays within a given tray will all have the same size sample. Exemplary trays have footprints to receive up to six standard SBS (Society for Biomolecular Screening) 8×12 racks and plates. The tray has a plurality of openings to permit containers to be accessed through the bottom of the tray as well as the top of the tray. The openings can have a large open center surrounded by a lip or ledge that catches the outer edges of an array plate to support the rack within the footprint over the open area, permitting access to the underside of the rack. Alternatively, the tray can have an array of smaller openings through an otherwise continuous bottom surface, with each opening corresponding to the position of a sample container, so that each container can be accessed through the opening.

Each sample, array and tray should be individually identified with a bar code or similar machine-readable indicator to permit tracking of each sample, and the arrays and trays will generally have an orientation indicator, such as a notched corner, to facilitate handling and tracking of the samples.

Figure 1:
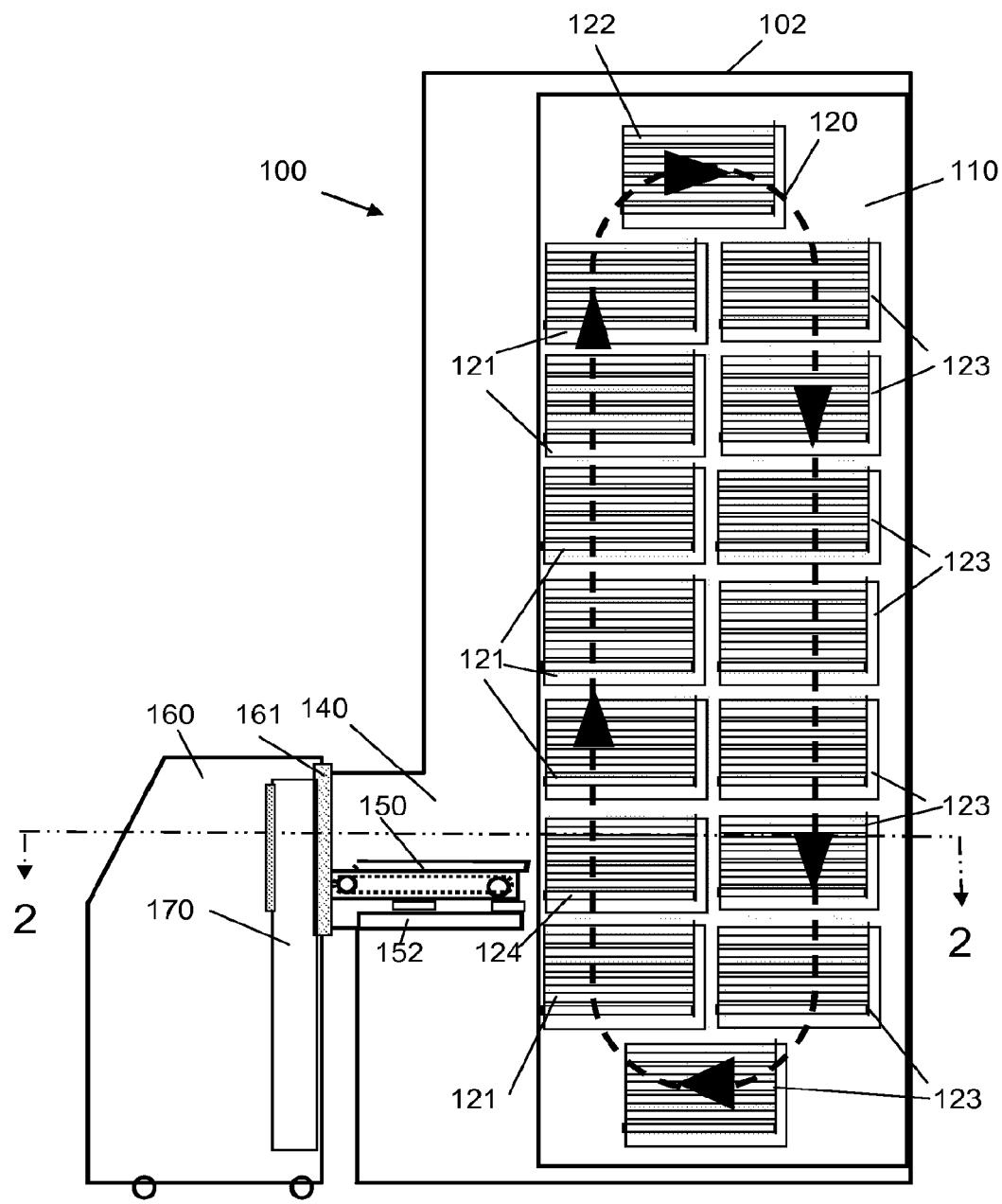
FIG. 1 is a diagrammatic cross-sectional side view of a first embodiment of the system showing the storage unit, shuttle and external modules.

A first exemplary embodiment of the automated sample storage and management system of the present invention is illustrated in FIGS. 1-3. The basic components of the system 100 include storage compartment housing 102, storage compartment 110, vertical carousel track 120, tray carriers 121-124, tray shuttle compartment 140, tray shuttle 150, modules 160, 162 and 164, and control station 170.

Figure 3B:
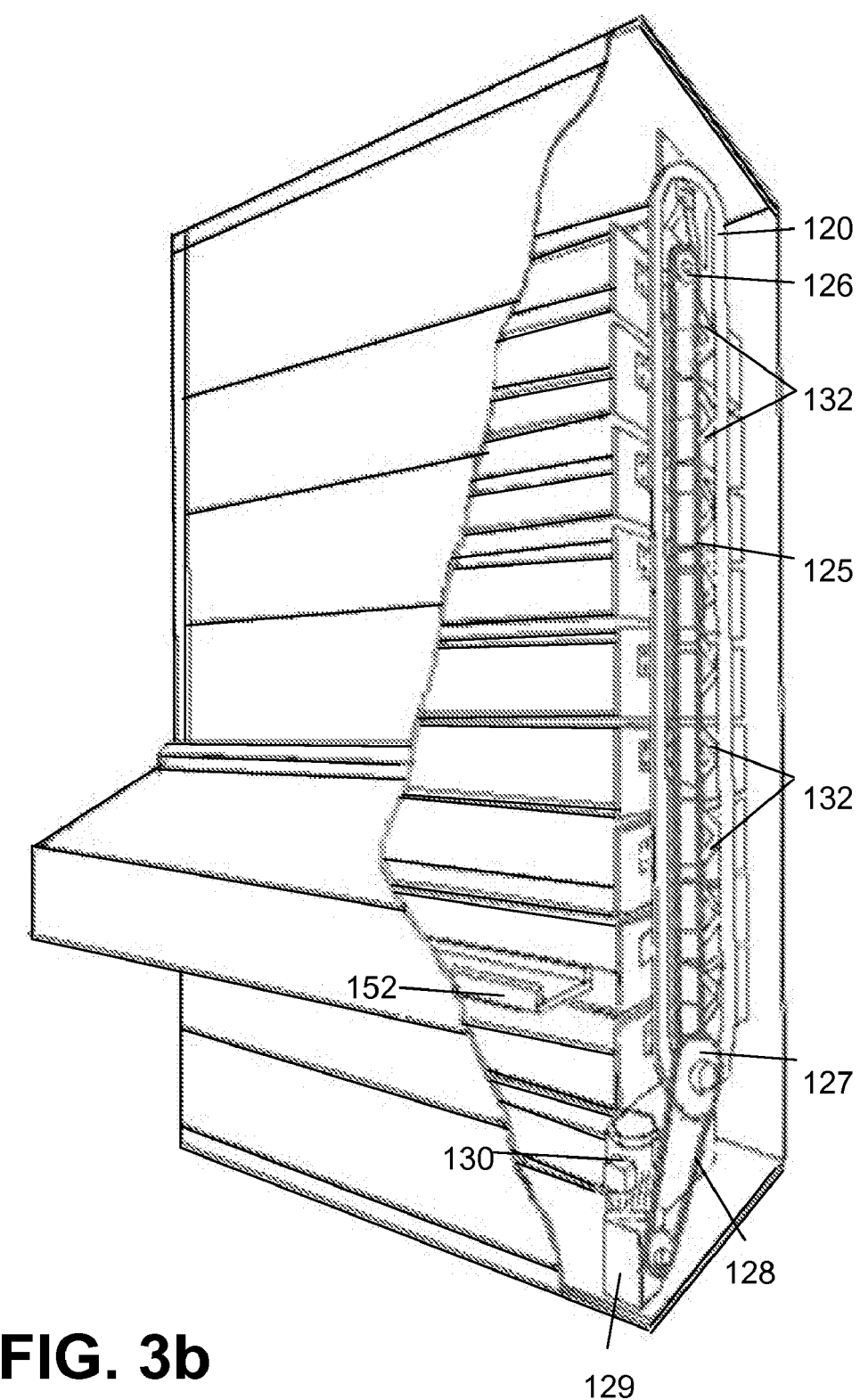
FIG. 3b is a diagrammatic perspective view with the housing partially cut away to show elements of the carousel mechanism.

The vertical carousel mechanism, which is commercially available from Remstar International, Inc. (Westbrook, Mass.), operates much like a Ferris wheel, and is capable of clockwise or counter-clockwise rotation while maintaining each tray carrier in an upright position. FIG. 3b illustrates primary components of the carousel including vertical carousel track 120, drive chain 125, upper drive gear 126, lower drive gear 127, transmission chain 128, transmission 129, and drive motor 130. As is known in the art, carrier guides 132, which are pivotably attached to the sides of the carriers and pivotably linked to drive chain 125, have guide arms that slide within carousel track 120 to keep the carriers upright throughout their travel.

Access to all trays in storage compartment 110 is obtained by activating the carousel to move the carrier 124 containing the desired tray, rack and sample into alignment with tray shuttle 150, which provides horizontal movement along plane 152 that extends perpendicular to, and across the front of, storage compartment 110 to permit access to every tray in carrier 124. The carousel controller is capable of halting rotation in either direction with sufficient precision to horizontally align not only carrier 124, but each individual tray with the shuttle 150. Shuttle 150, which is described in more detail below, also provides horizontal movement toward and away from storage compartment 110 to allow trays to be pushed into or pulled from slots in carrier 124.

Each carrier 121-124 in the carousel is a four-sided shelf, with panels on the bottom, back and two sides, with multiple vertical partitions 322 (shown in FIG. 3*a*) to define a plurality of tray supports. (Note that the partitions 322 are shown only in carrier 122 for ease of illustration, but each carrier will have multiple partitions, with the number of partitions depending on the tray widths and the widths of the carriers.) Each vertical partition 322 has a plurality of tray support slots (inwardly extending channels or ledges) separated by a width corresponding to the widths of the trays, so that the trays are supported parallel to the bottom of the carrier. The slots are configured to permit sufficient clearance between vertically adjacent trays to accommodate a variety of different size (height) racks and samples. The versatile slot configuration is achieved by utilizing a standardized tray thickness for all types of arrays (racks and plates), regardless of the height of the container. The vertical partitions are formed with uniformly spaced horizontal ribs or rails extending the entire height of the partition 322, as illustrated in FIG. 3*c*. The dimensions of the tray slots 324 are such that the standard thickness trays 326 can be easily slid into and out of the appropriate slots to provide sufficient clearance between the various size racks 328, 329, 330 that can be retained on the trays 326.

The independent vertical and horizontal motion of the carousel and the tray shuttle permit more rapid access of samples that may be distributed throughout the storage compartment. Retrieval times can be minimized by activating the carousel while the shuttle is transporting a tray to a processing module, so that once the shuttle has transferred the retrieved tray to the module, the next carrier and tray will already be horizontally aligned with the shuttle so that the shuttle can immediately move to the correct horizontal position to pull the next tray.

Also part of the storage system, but not described or illustrated herein, are the refrigeration equipment and temperature control and monitoring instrumentation. Such components are well known in the art and selection of appropriate components will be readily apparent to those in the field.

One or more modules 160, 162, and 164 are located on the front of tray shuttle 150, on the opposite side from storage compartment 110. Each module is capable of receiving one or more trays from the tray shuttle and performing some operation on the trays, such as modifying the contents of a particular tray, cherry picking specific samples from a tray and placing them in another tray, defrosting a tray for prior to removal of the samples for use, inspection of the samples, or interface with and transfer samples to another storage system or material processing station. This modular configuration allows the system user to customize the system to their own specific needs. For example, multiple cherry picker modules may be provided, with one module for selecting vials and another for selecting tubes. In an exemplary combination, module 160 is a vial selector, module 162 a tube selector and module 164 an input/output-defroster. Other combinations of cherry picker modules can include vial selectors for different size vials, or plate selectors which can remove specified plates from source trays and combine them with other selected plates in a destination tray. The modules can be insulated and have a controlled atmosphere, including being cooled to the same temperature as the tray shuttle compartment 140 and/or filled with a gas to create an inert atmosphere.

I/O-defroster module 164 is preferably supplied with well-stirred, heated air to maintain the maximum heated air temperature and overall cabinet temperature within a tightly regulated range. This enables rapid thawing without risk of hot spots that can overheat some samples. Module 164 includes an access door 167 for removing trays from, and replacing trays into, the module. A bar code reader 165 or other tracking device within module 164 automatically reads and records the identities of every tray, rack and, if possible, sample container, that passes through the module and forwards these identities to system controller 170. System controller 170 will track trays removed from the system by checking them out and checking them back in when they are inserted back into module 164 and reloaded by the tray shuttle to ensure that the location of every sample, rack and tray is known at all times and to prevent inadvertent placement of a tray in an incorrect position in the storage compartment when the samples are returned to storage.

While the I/O module 164 is capable of reading and recording the bar codes on trays, and racks, it can be difficult to read a bar code that is affixed to a round bottle or vial since the container can rotate, directing the bar code away from a optical reader in fixed position. Conventional automation techniques will rotate the bottle by some means so that the barcode will at some point pass in front of a fixed reader. Rotating devices add expense and are generally slow.

Vial picking module 160 includes an assembly for rapidly reading bar codes on vials without rotating the vial using a combination of a conventional fixed position reader and mirrors that are positioned to permit reading of the entire surface of the vial. In the case where the vial is already being moved by a robot, no additional mechanics may be required.

Figure 15A:
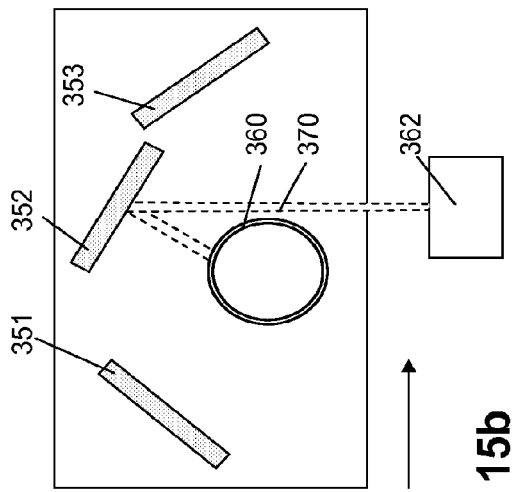
FIGS. 15a-d are diagrammatic top views of a series of reading steps to allow a fixed bar code reader to view the right, right rear, front, and left rear sides of a sample vial, respectively.
Figure 15B:
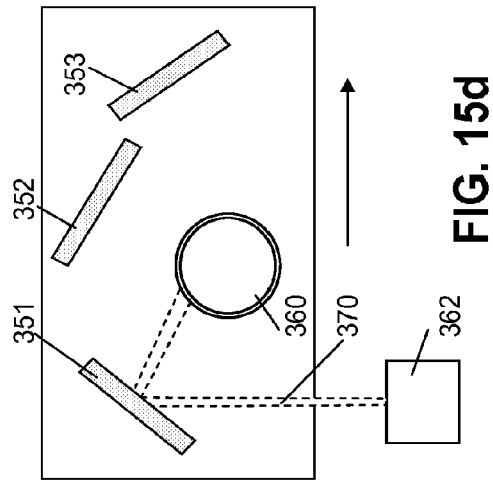
Figure 15C:
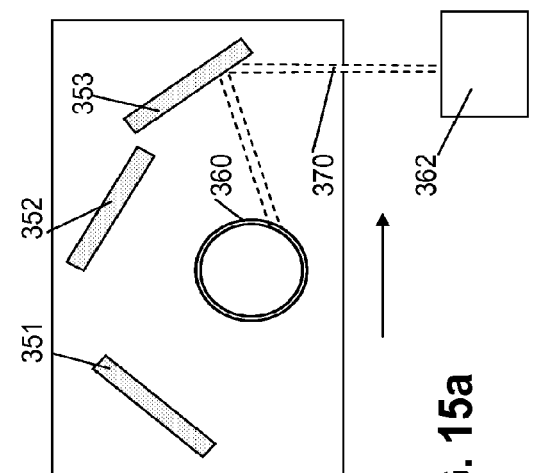
Figure 15D:
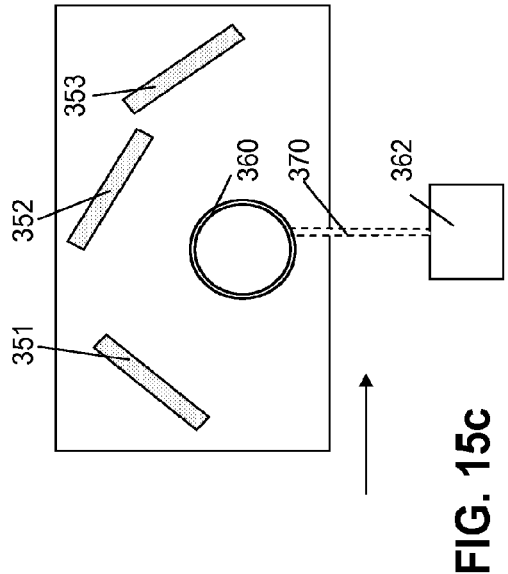

Vial picking module includes a vial pick head with an automated claw-like mechanism that grasps only top of the vial, so that the portion of the vial bearing the bar code extends down from the pick head. Such mechanisms are generally known in the art. FIGS. 15*a-d* illustrate how three mirrors 351-353 can be attached to move along with the vial pick head to reflect reading beam 370 to view different sides of vial 360, allowing a fixed position bar code reader 362 to used. Beam 370 is projected continuously forward. As the pick head, holding vial 360, with attached mirrors 351-353 is translated left to right (as illustrated), the first position, shown in FIG. 15*a*, aligns mirror 353 with beam 370, allowing the right side of vial 360 to be read. In FIG. 15*b*, pick head continues is translation, placing mirror 352 into position to reflect beam 370, allowing the right rear side of the vial to be viewed by fixed reader 362. FIG. 15*c* illustrates the pick head moved so that beam 370 directly impinges upon the front of vial 360. FIG. 15*d* shows the pick head in a position so that beam 370 is reflected by mirror 351 to view the left rear side of the vial. These four different positions permit all sides of the vial to be viewed with small amounts of overlap such that at least one of the positions will produce a signal corresponding to the vial's ID. Since the only moving part is the pick head and its translation mechanism, if the reader has not detected a bar code after a single pass, the pick head can be reversed to a starting position, then activated to repeat its path past the reader.

The lack of moving parts, other than the single axis translator, provides for a robust reading system. Different configurations of mirror may be also used. For example, two flat mirrors may be used to view the entire area but with no overlap, or one shaped mirror could be used. The mirrors can be positioned at some distance from the vial to provide sufficient clearance for clamping mechanisms or other moving elements. In an alternate configuration, the reader can be moved (or rotated) relative to the vial and mirror assembly, which is stationary.

Figure 16:
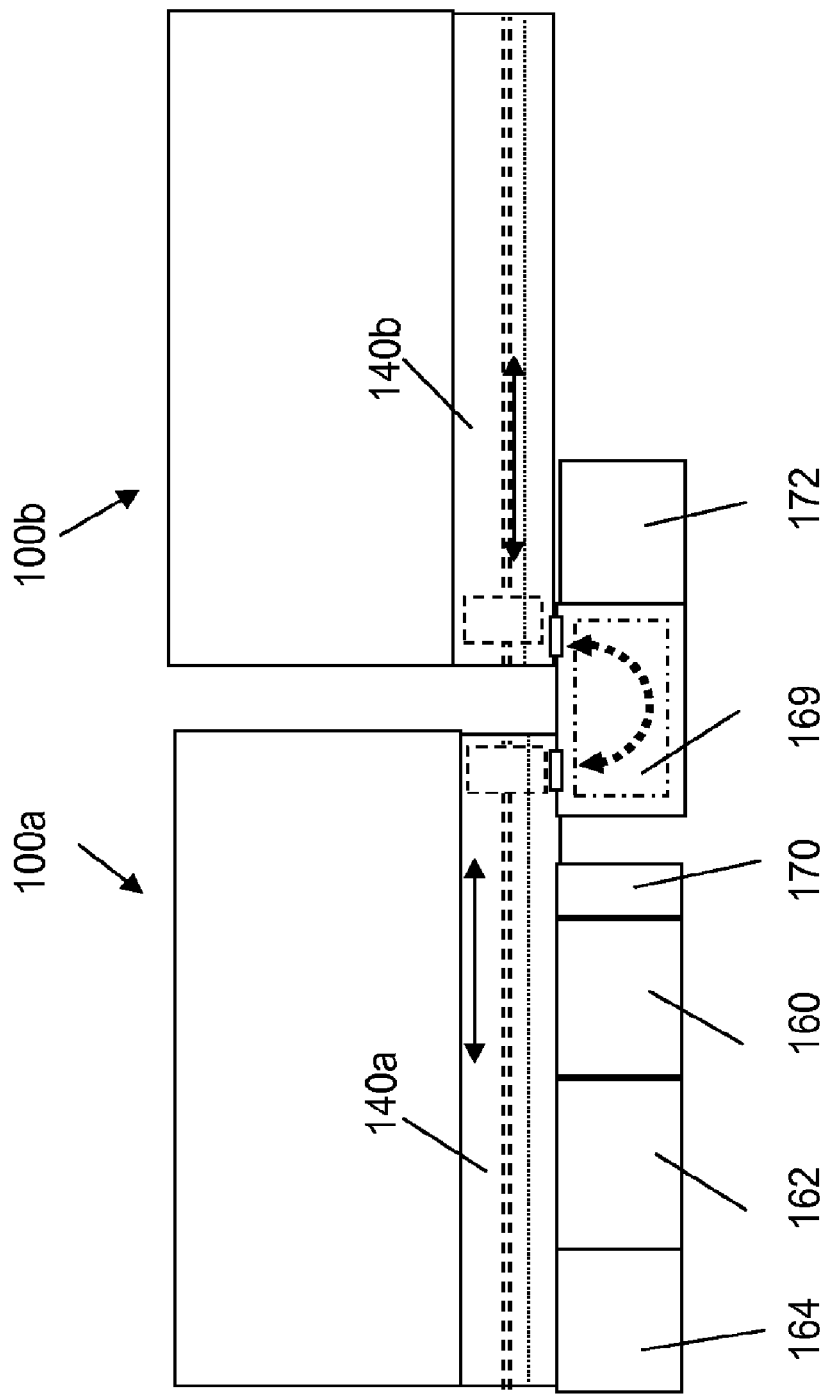
FIG. 16 is a diagrammatic top view of two storage systems bridge together using a bridge module.

Yet another possible module for use with the inventive system is a bridge module, which is illustrated in FIG. 16. As shown, bridge module 169 is attached to the front of tray shuttle compartment 140a at the right end of the row of modules 160, 162, 164 of a first storage system 100a. Bridge module 169 extends beyond the right end of system 100a and attaches to the front side of tray shuttle compartment 140b of second storage system 100b. This inventive design permits a system user to expand their storage capacity (double, triple or more) without disturbing an existing storage system. Current commercial systems require the storage compartment to be compromised if the system owner wishes to expand the capacity of an existing system rather than purchase a new, larger system. This permits the system user to purchase the more economical system for its currently needs and expand at a later date as needed by purchasing one or more additional systems. The interface between the two bridged storage systems permits rapid access to all samples within all systems, allowing samples to be selected from either system to perform selection and transfer of samples into a common destination tray. The second storage system 100b can have its I/O module 172 as shown, or it can transfer a retrieved tray from tray shuttle 140b through bridge module 169 to tray shuttle 140a and to I/O module 164. Preferably, module 169 will include a bar code reader to track trays, racks and samples that may be moved from one storage system to the other.

An additional module, with a similar function to that of the bridge module can serve as an automation interface for transferring trays, racks and samples to separate material handling workstations without manually removing the tray from the storage system to transport it for additional processing or high-throughput screening. An exemplary commercially-available workstation is the BioCel Series Automation System (Velocity 11, Menlo Park, Calif.). The interface module can be positioned in a similar manner to bridge module 169, with the workstation located slightly to the side of the storage system, or it can be positioned so that the workstation is in front of the storage system, with the automation interface module sandwiched between the storage system and the workstation.

Each module is releasably connected to the front side of tray shuttle compartment 140 by way of a small opening that is sealed with a gasket 161. The modular construction of the storage system permits modules to be removed or serviced without disrupting the frozen environment of the stored samples. During servicing, or when modules are exchanged, the opening between the removed module and the tray shuttle compartment can be sealed with a dummy plate.

Figure 14:
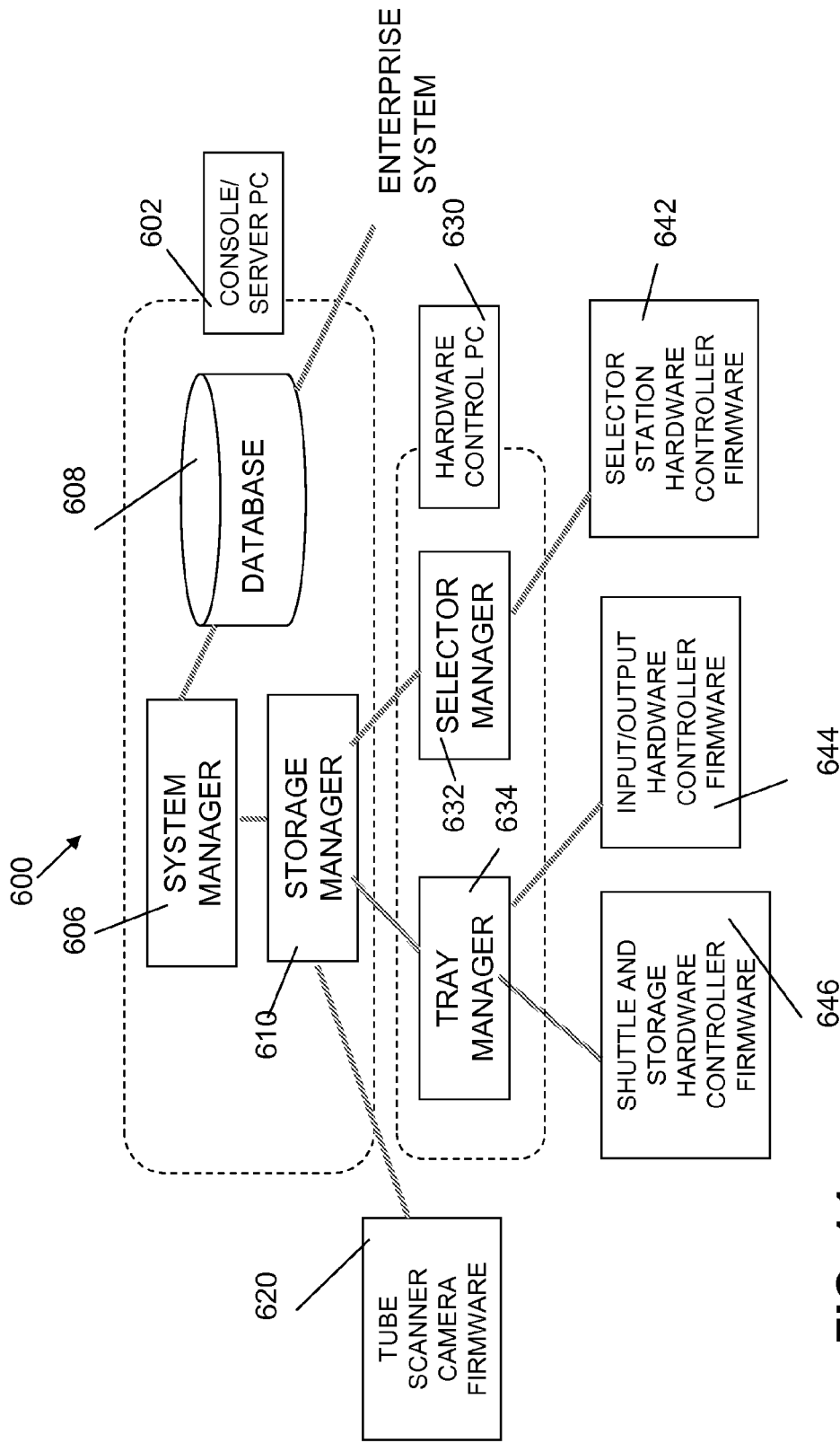
FIG. 14 is a block diagram of software and firmware elements of the controllers of the storage system.

The processing of samples typically occurs within an enclosure on the upper portion of each module. Below the processing enclosure of each module is a cabinet that encloses the hardware components for controlling each module and the interfaces between the modules and the tray shuttle. The software/logical architecture 600 of the system is shown in FIG. 14. Each module has its own dedicated hardware controller 642, 644, 646, and each of these controllers is driven by a hardware control PC 630 which runs selector manager 632 and tray manager 634 software for controlling cherry picking and tray transport by the tray shuttle, respectively. A console/server PC 602 includes software for system management 606, storage management 610 and communication with a database 608 containing information about each sample that is or has been in the system. PC 602 also provides an optional connection to an enterprise system via a network switch as well as interfacing with a video controller 620 that operates a video camera (not shown) for visually tracking operations in each of one or more modules. Each PC 602 and 630 is powered by a UPS (uninterruptible power supply) (not shown) that is also housed within the cabinets in the bottom of the modules.

Additional modules can include liquid handling devices that can receive a defrosted tray, and at room temperature, preferably in an inert atmosphere, de-cap the containers, then aspirate and dispense a portion of the sample. The samples can then be re-capped without requiring removal of the storage tray from the system. An exemplary capper/de-capper system is disclosed in co-pending U.S. application Ser. No. 11/555,621, which is incorporated herein by reference.

Figure 11A:
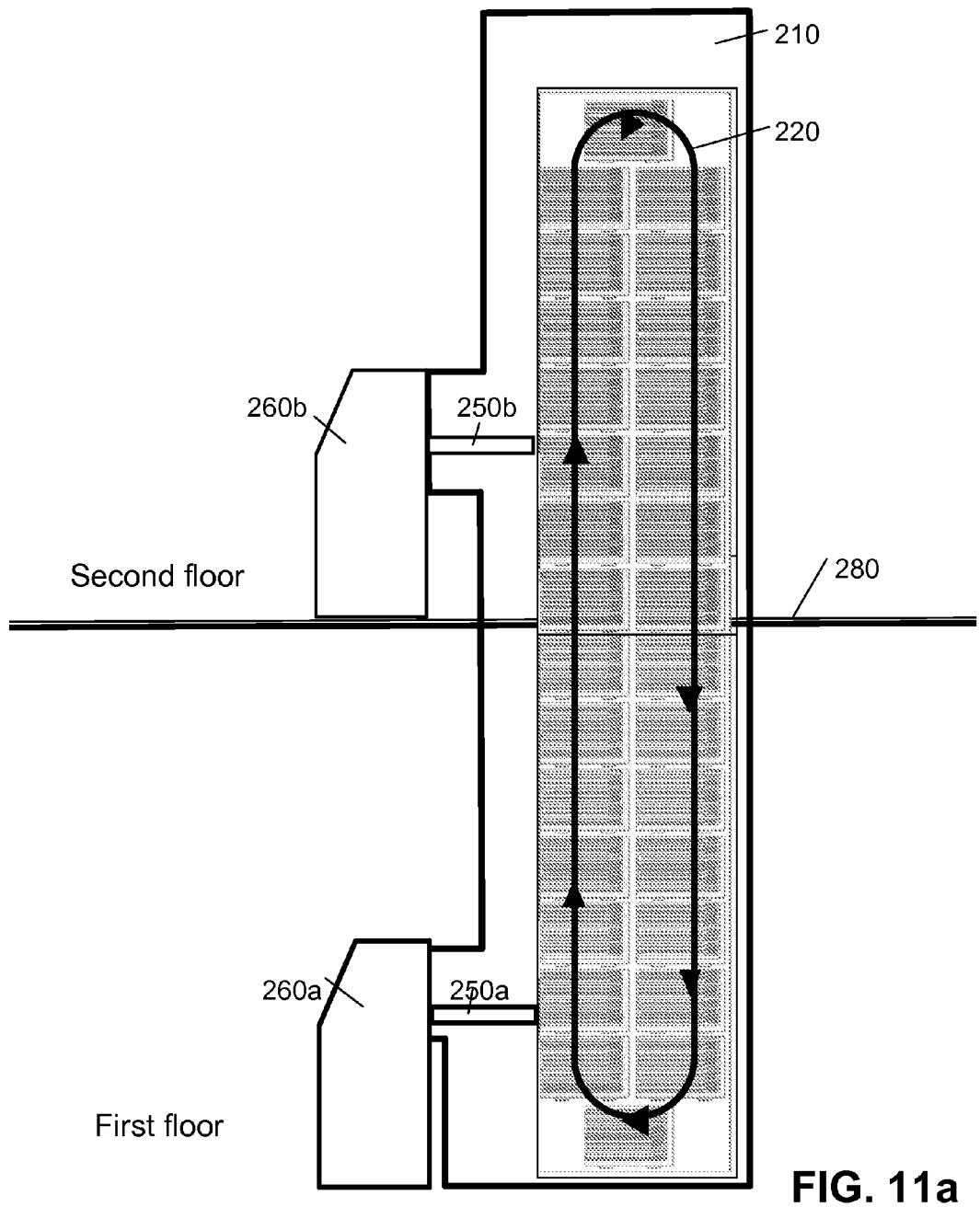
FIG. 11a is a diagrammatic side view of a multi-story system with flexible access modules.
Figure 11B:
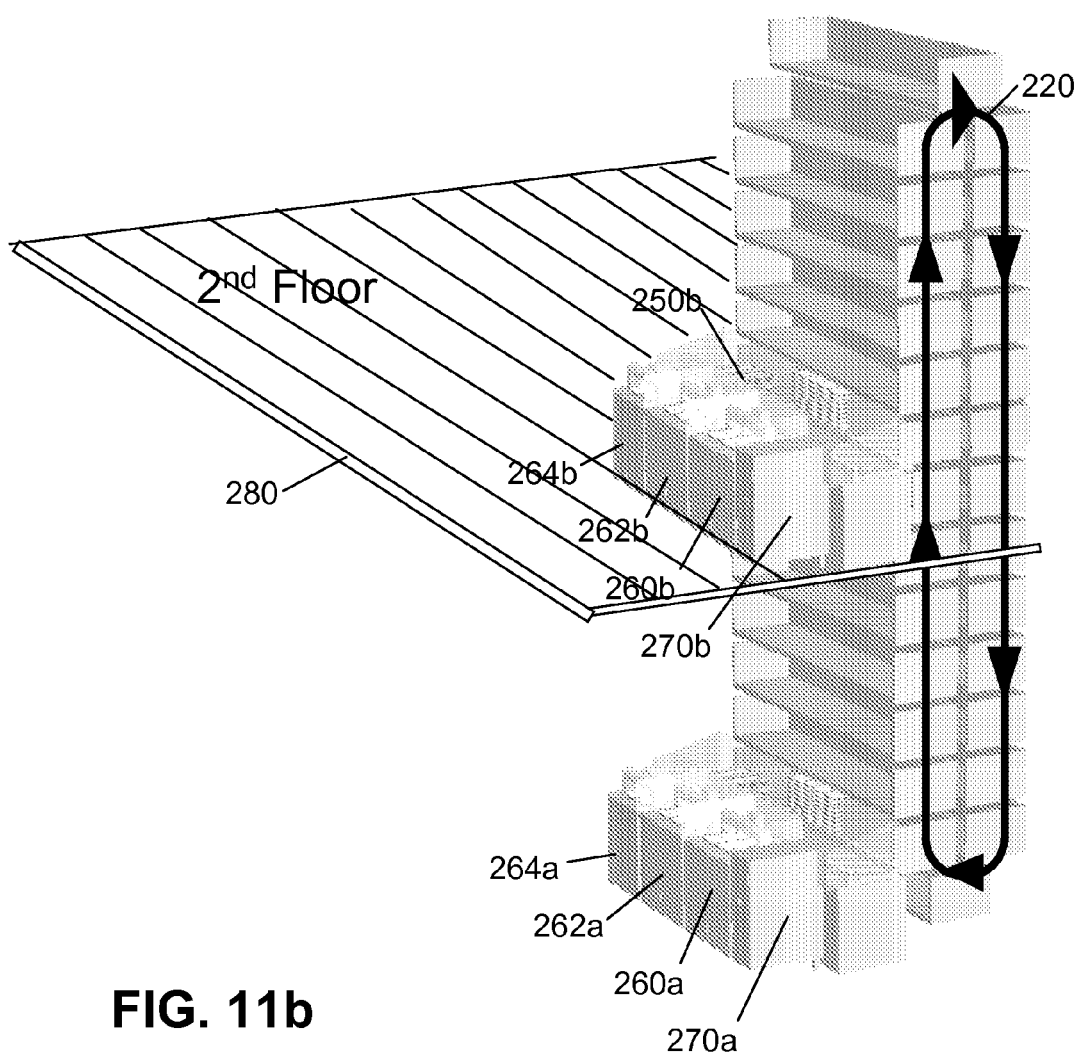
FIG. 11b is a perspective view of the multi-story system with the housing removed to show the vertical carousel.

The modular design permits the system to be accessed at different elevations along the height of the vertical carousel in addition to or other than the base of the system, which is particularly advantageous for multi-story storage systems. An exemplary set-up is illustrated in FIGS. 11a and 11b. Storage compartment 210 and vertical carousel guide 220 span two stories, passing through the floor 280 that separates the two stories. Each floor has its own tray shuttle 250a and 250b, its own controller 270a, 270b, and its own combination of processing modules 260a & b, 262a & b and 264a & b. By providing an opening on a second, third, or other floor, different laboratories can have localized access to a common storage compartment while utilizing processing modules that are particularly suited to their needs. Software in the system controller will prioritize requests for access in situations where requests are submitted at or near the same time from different laboratories.

In situations where space is available in a basement for installation of the storage compartment, but where access would be inconvenient or undesirable, the system can be configured to have access points only on the first and/or second floors with no access point in the basement. This can add considerable storage capacity without taking up valuable laboratory floor space.

In multi-story systems, it may be desirable to incorporate a sensing device and a small amount of Z-axis positioning to accommodate shifting or settling of the building structure and floors relative to the storage system so that the tray shuttle remains in proper alignment with the carousel. These changes are typically small and occur over long periods of time, so the throughput of the system is not affected. The modules are coupled to the system in a way as to allow this small movement without disturbing the seal.

In an alternate embodiment (not shown), a multi-story or single story storage system can be modified to provide access to a second laboratory located in a different room by attaching a tray shuttle compartment to the back side of the storage compartment. The access points could be on the same level or at different levels since the tray shuttle interacts only with the immediately adjacent carrier. In this modification, the carousel carriers would be open on the front and the back, allowing trays to be removed from either side of the carriers. Both laboratories would have their own processing modules, which would provide more rapid access to samples.

Referring back to FIGS. 1-3, each of the modules 160, 162 and 164 is capable of independent operation, allowing multiple operations on different samples to be performed in parallel, and at least some of the modules include the ability to handle multiple trays at one time. This allows removal or replacement of trays in a module while the module operates uninterrupted. For a selector, or "cherry-picking", module as illustrated in FIGS. 9a and 9b, two source tray 920, 921 positions are provided on pick table 901 so that while the mechanism picker 902 is selecting samples from one tray 920, the other source tray 921 can be returned to storage and replaced with a different tray. The single destination tray 950 is replaced as it is filled. This technique allows the picking rate to be considerably faster than existing methods because there is no down-time for the picking mechanism.

In an alternate embodiment of the storage compartment that is particularly suitable for ultra cold storage, the vertical carousel is replaced by stationary racks 520 and a gantry operated tray shuttle 452, capable of vertical and horizontal movement, that is housed within a higher temperature (~−20° C.) compartment. An exemplary gantry mechanism is disclosed in U.S. Pat. No. 6,663,334, which is incorporated herein by reference.

Figure 4:
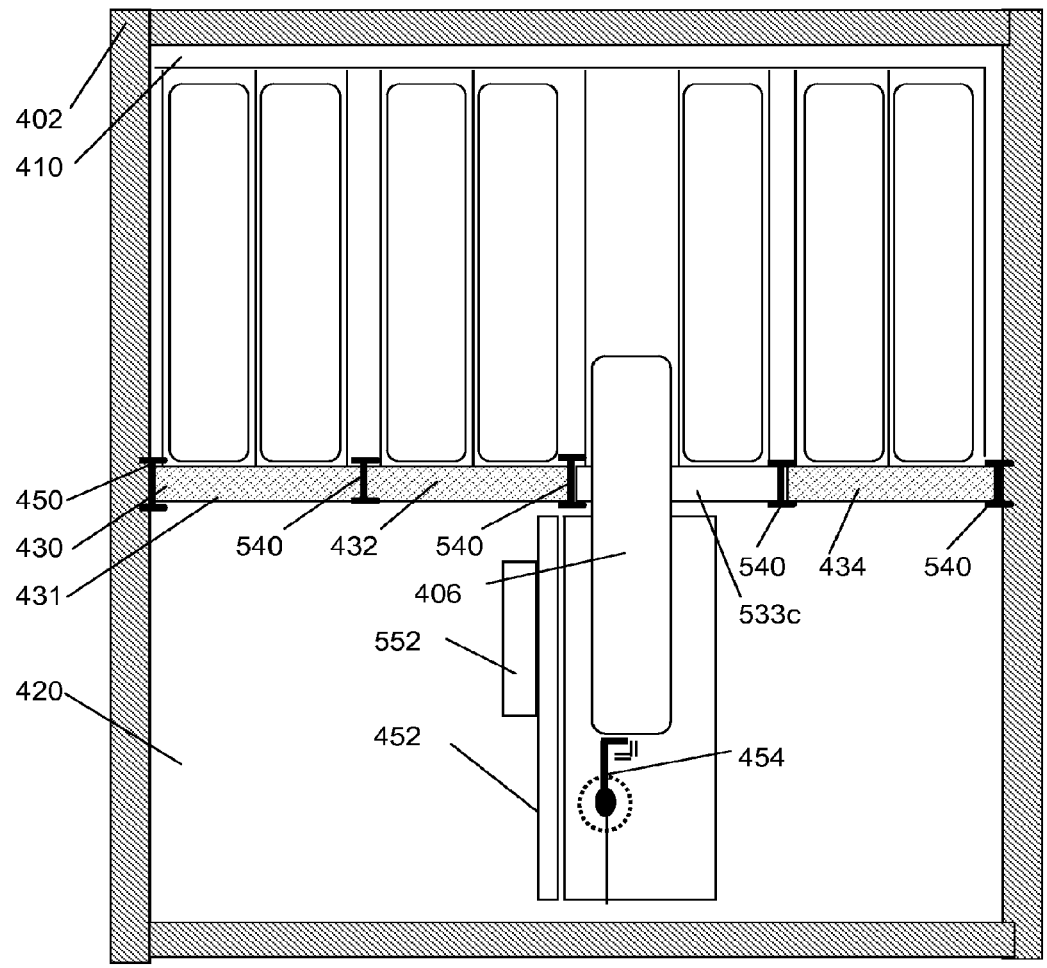
FIG. 4 is a diagrammatic top view of a second embodiment of the system with an insulating wall separating the storage compartment from the tray shuttle.
Figure 5A:
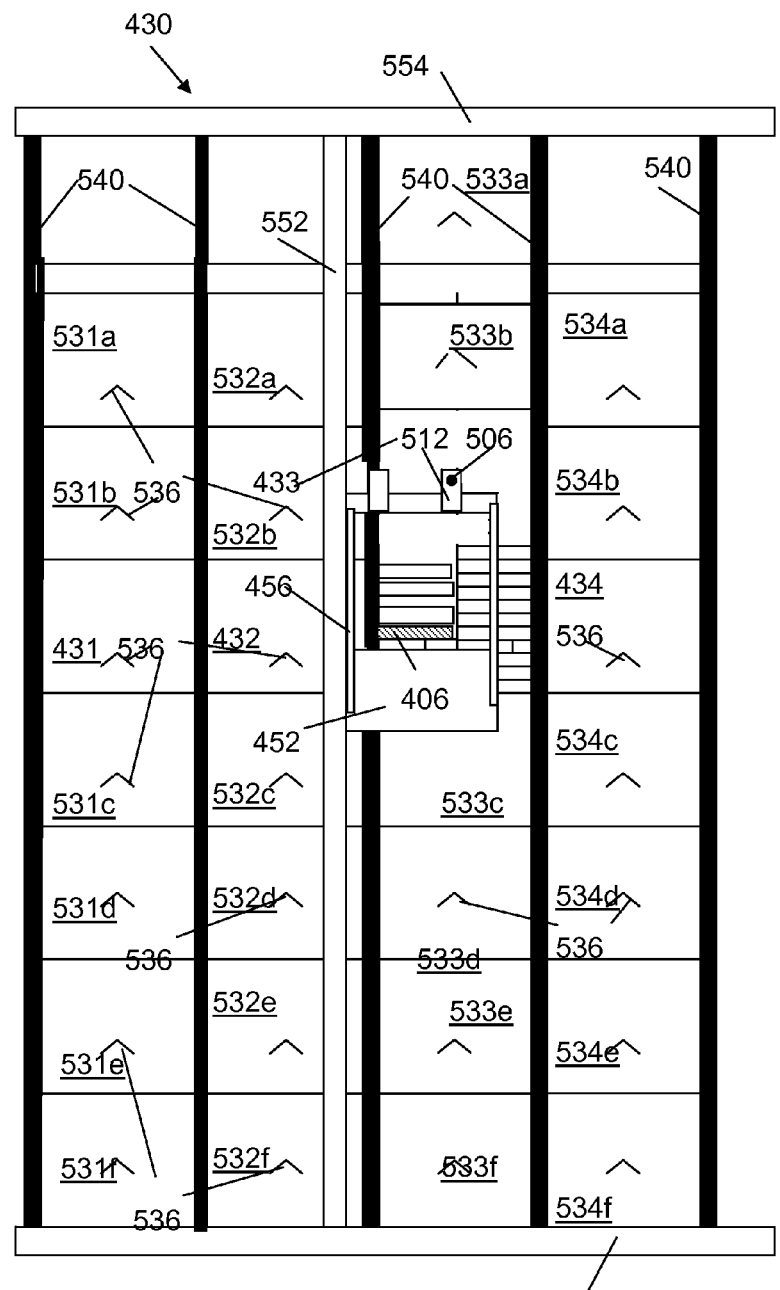
FIG. 5a is a diagrammatic front view and FIG. 5b is a perspective view with the housing partially cut away, both showing the tray shuttle and insulating wall according to the second embodiment.
Figure 5B:
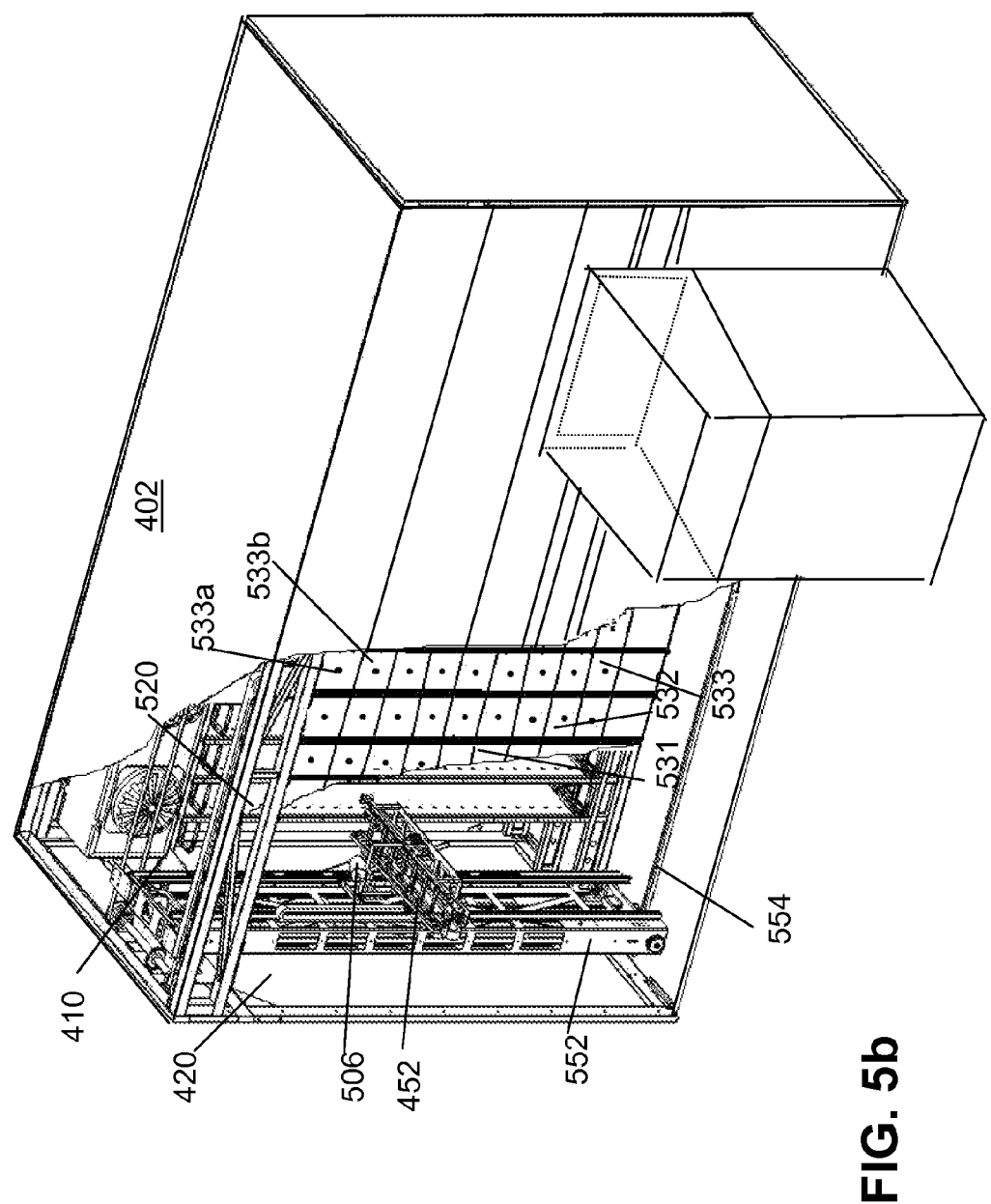
Figure 6A:
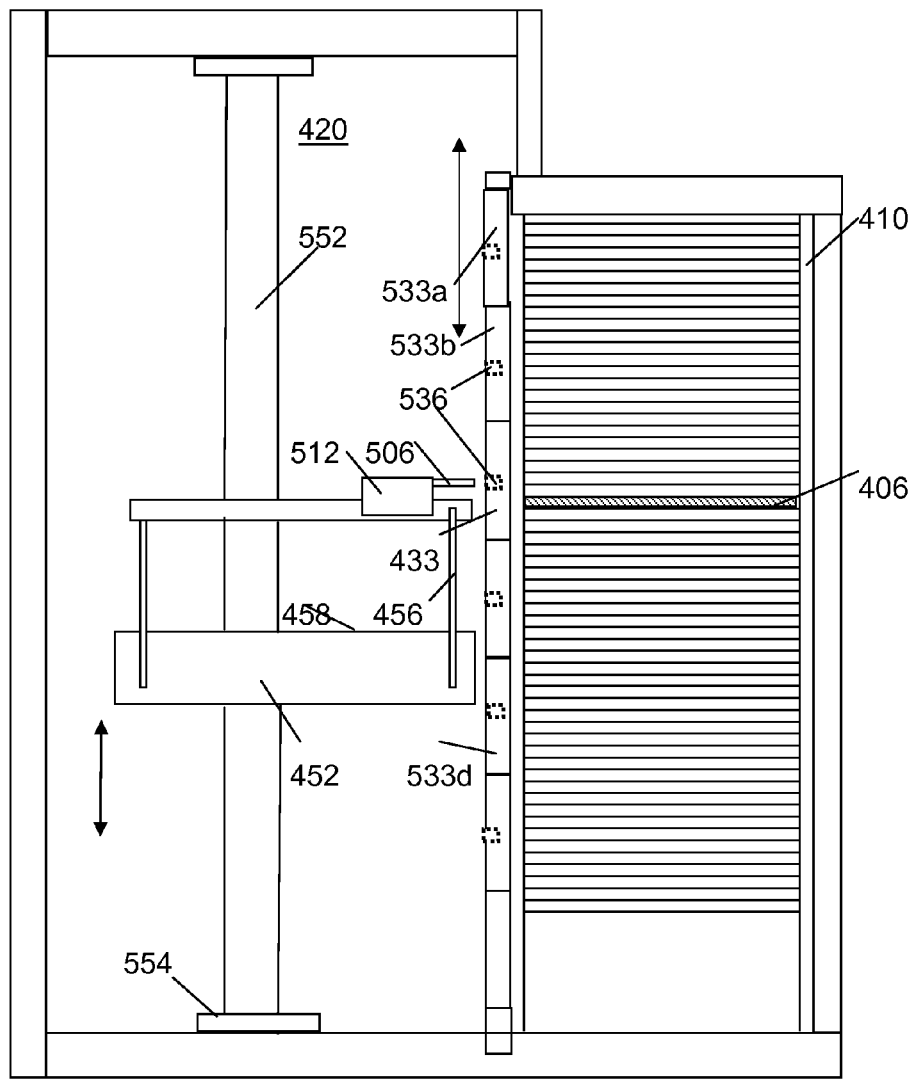
FIGS. 6a-6c are diagrammatic side views of the second embodiment showing the steps for accessing and removing a tray from the storage compartment by lifting the insulating.
Figure 6B:
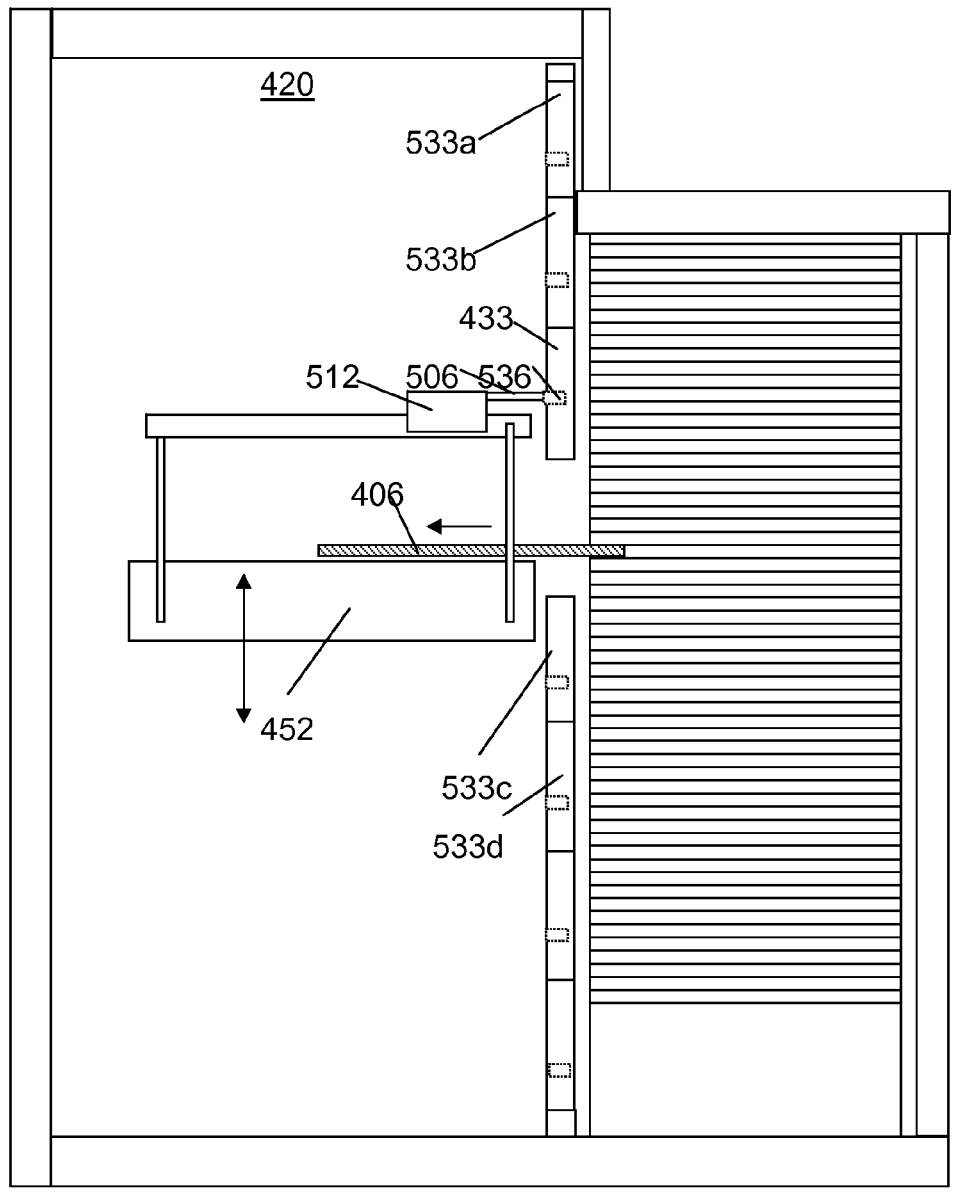

As illustrated in FIGS. 4-6, within storage system housing 402, storage compartment 410 is separated from tray shuttle compartment 420 by a wall 430 formed from stacks or columns of individual foam bricks or blocks (431-434 in FIG. 4 plus 531a-f, 532a-f, 533a-f, and 534a-f, in FIGS. 5a and b) that are arranged to create a robotically friendly insulating wall 430. The blocks are arranged in stacks and held in place by gravity. Guide rails 540 on each side of the stacks constrain the blocks against lateral movement while allowing them to slide up and down freely. As illustrated in FIG. 6a, to access a specific tray, gantry 552 moves horizontally along gantry rail 554 and moves robotic tray shuttle 452 vertically to align it with block 433 in front of the desired tray 406. Pin drive mechanism 512, extends pin 506 into a corresponding recess 536 in block 433, the tray shuttle 452 moves upward on gantry 552 to lift block 433 and all other blocks 533a, 533b above that point, as shown in FIG. 6b. In the embodiment illustrated, pin 506 is held at a fixed height above the tray support surface 458 of tray shuttle 452 by columns 456, so the system controller will be able to determine exactly how much block 433 needs to be lifted to obtain access to tray 406. In an alternative embodiment, a separate lift motor can be provided on tray shuttle 452 to move horizontal drive mechanism 454 vertically relative to tray support surface 458.

Figure 6C:
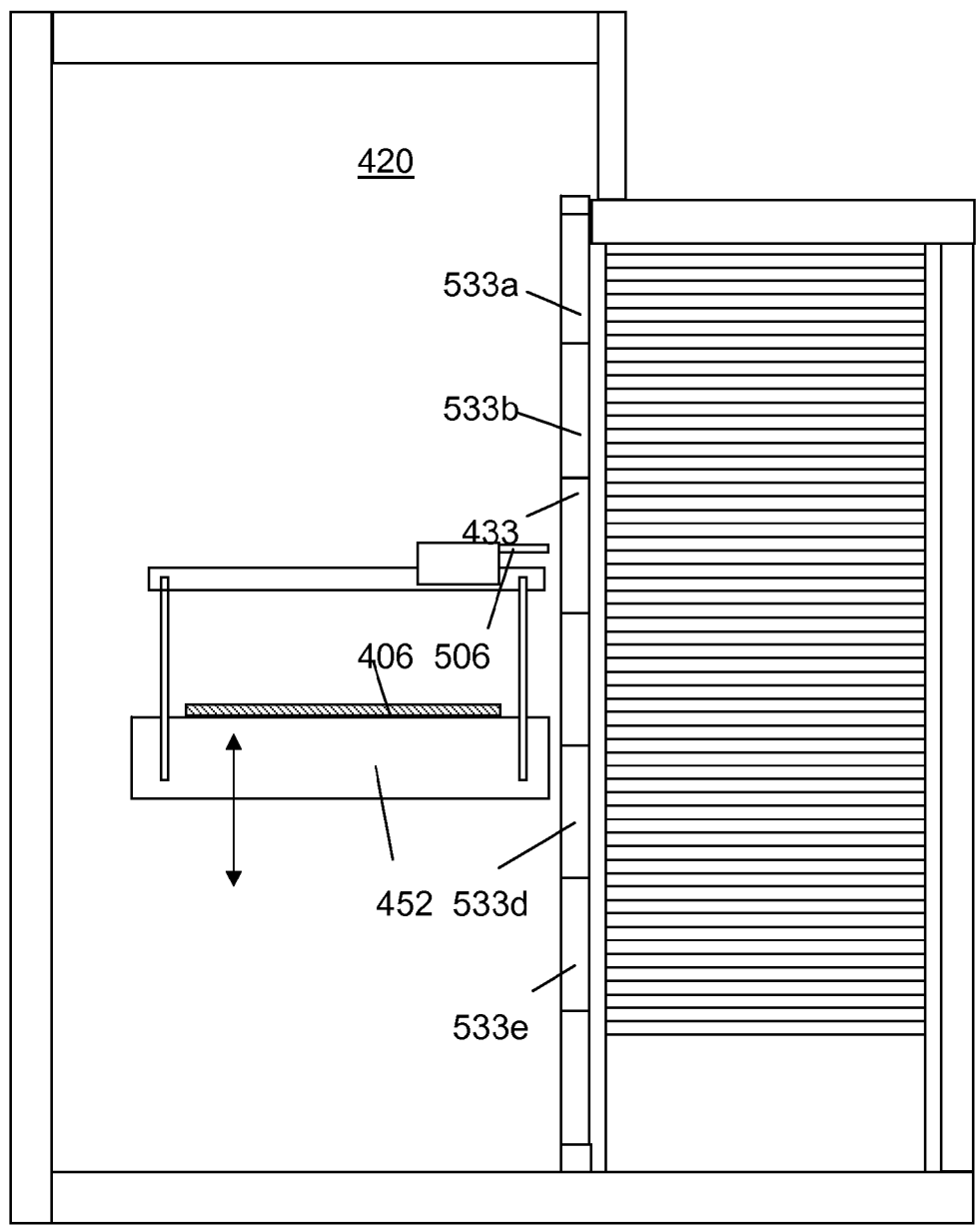

The tray of interest 406 is extracted by using tray hook 454 (shown in FIG. 4) to position the tray on tray support surface 458 of tray shuttle 452. As illustrated in FIG. 6c, tray 406 has been fully withdrawn, tray shuttle 452 is lowered to reposition blocks 433 and 533a & b into their original position, and pin 506 is withdrawn, restoring the insulating partition between the storage compartment 410 and the tray shuttle compartment 420. The blocks that make up the insulating wall can be of any size but it is preferable to keep them relatively small to minimize size of the gap created to access the desired tray position and, thus, minimize any temperature change that might occur when a gap is temporarily opened in the wall. The inventive approach allows the opening to be immediately closed after the tray is extracted, which provides a significant advantage over prior art systems that require a substitute tray be retrieved and used to plug the hole left by the extracted tray.

Figure 7A:
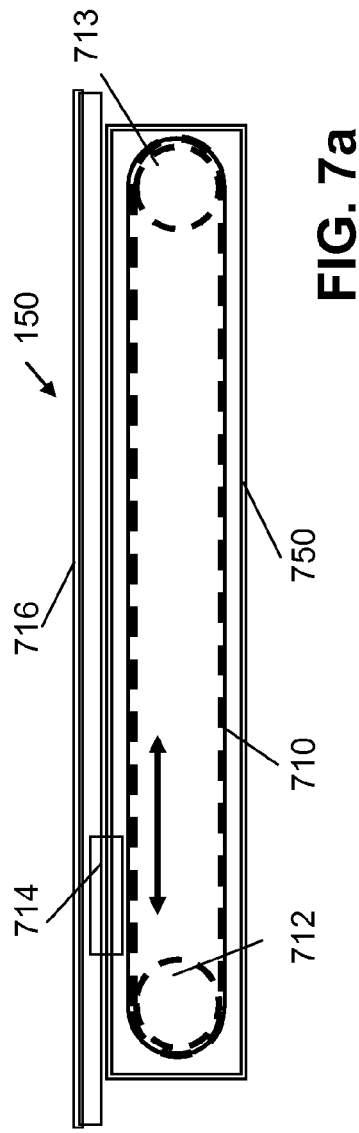
FIGS. 7a and 7b are diagrammatic side and end views, respectively, of the tray shuttle.
Figure 7B:
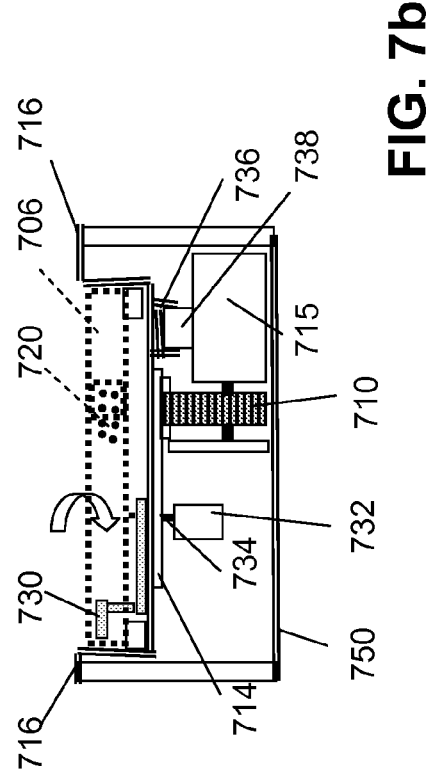

FIGS. 7a and 7b illustrate the elements of tray shuttle 150, which include shuttle frame 750, slide 714 which moves longitudinally along frame 750 in response to activation of belt 710, drive wheel 712 and belt guide 713, drive motor 715 which rotates drive wheel 712 clockwise and counterclockwise to activate belt 710 to move slide 714 forward and backward toward and away from the storage compartment. Slide guide rail 738 extends upward from frame 750 to cooperate with slide guide channel 736 on the bottom of slide 714 for repeatable motion. Extending from the top of slide 714 is tray hook 730, which rotates around axis 734 when activated by tray hook motor 732, which is attached to the bottom of slide 714. Tray hook 730 is configured to engage tray end hook 720 that extends from each end of tray 706 (indicated by dashed lines) when moved into contact with end hook 720.

Figure 8A:
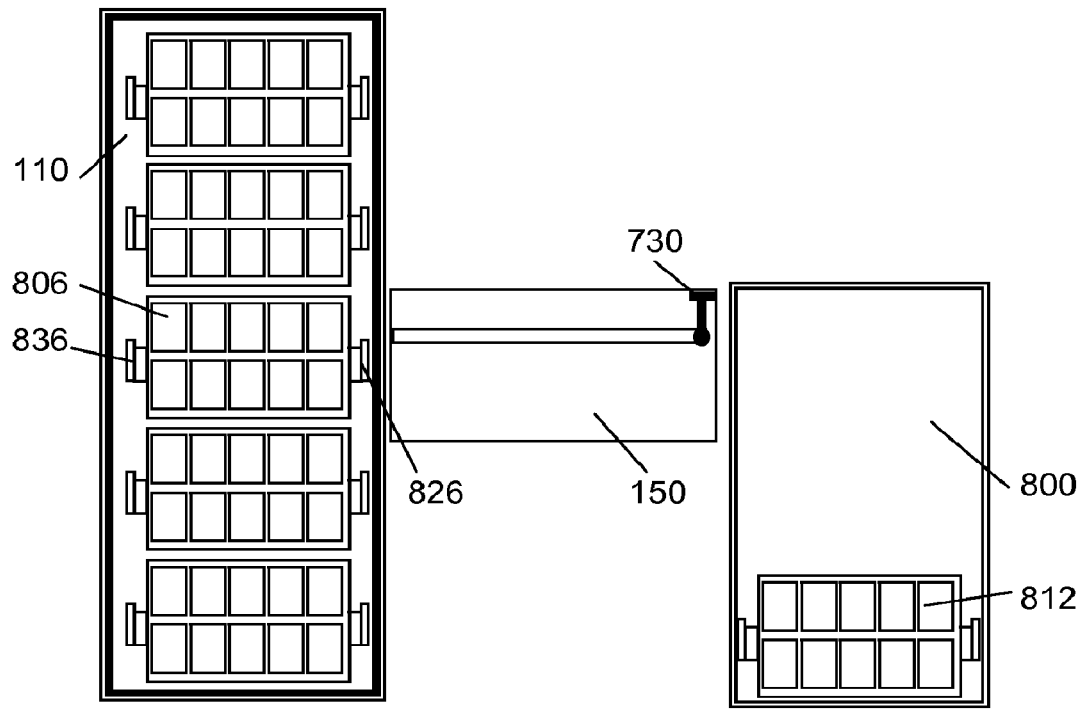
FIGS. 8a-8n are a series of diagrams showing the tray hook sequence through which trays are retrieved from the storage compartment and delivered to a module at the front of the system in preparation for cherry picking of specific sample containers.
Figure 8B:
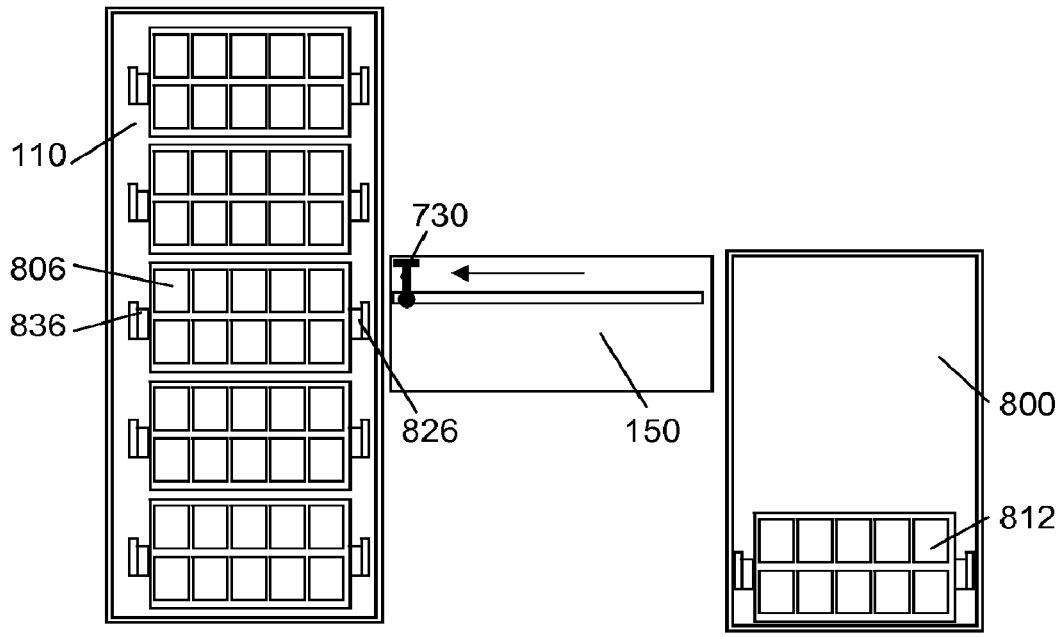
Figure 8C:
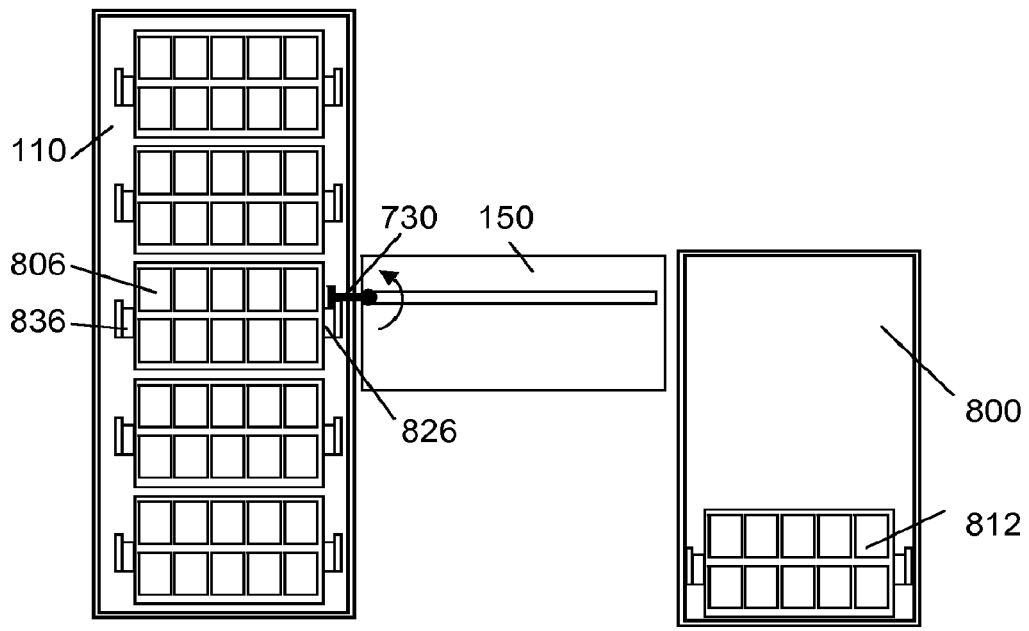
Figure 8D:
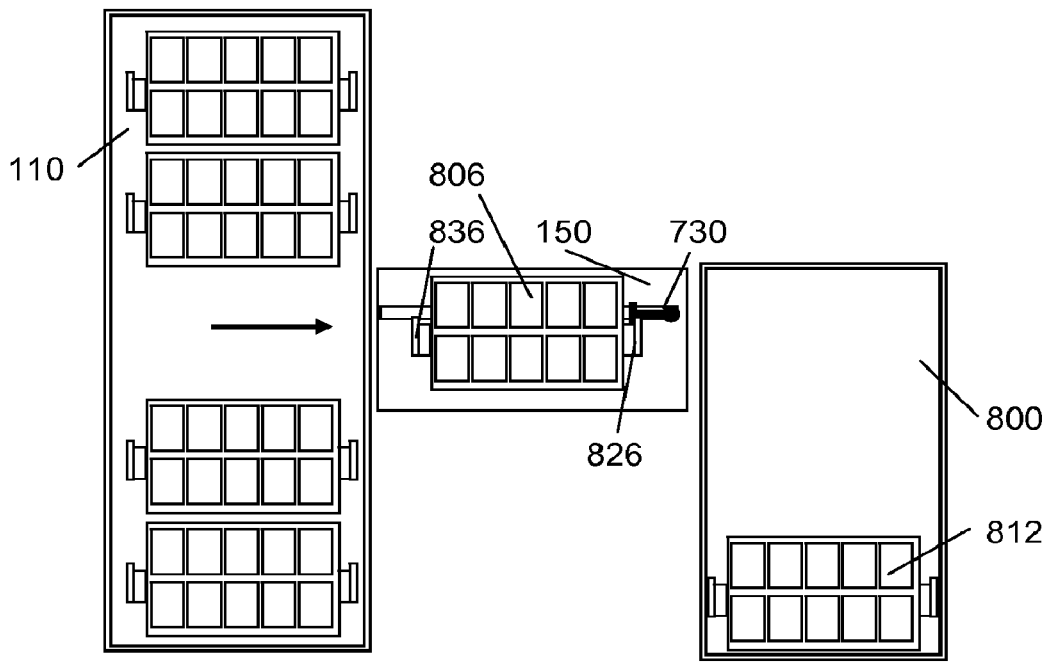
Figure 8E:
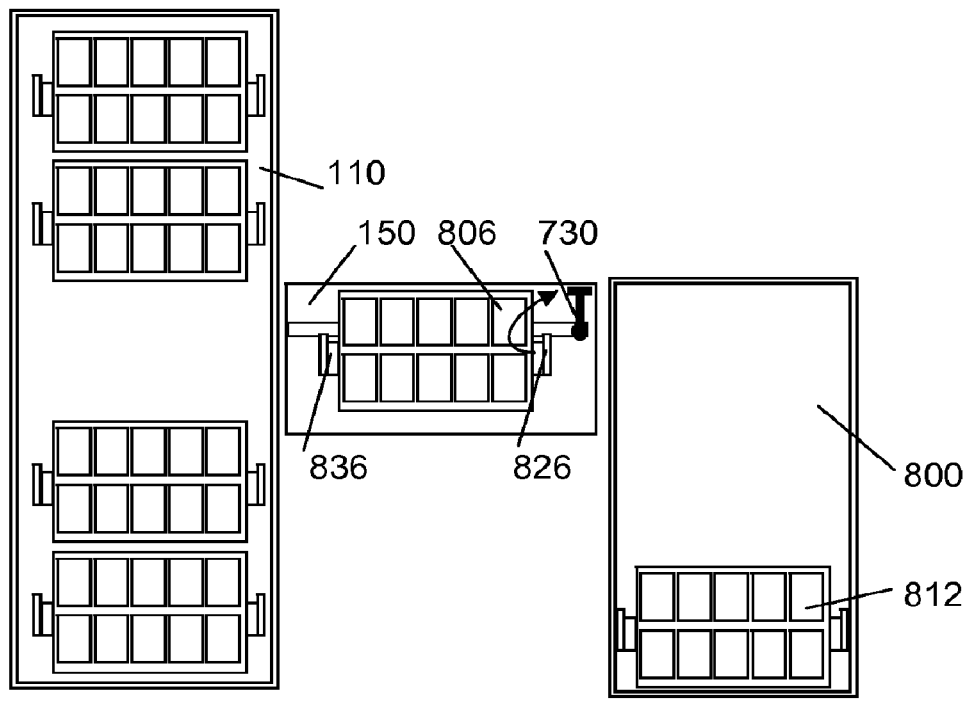
Figure 8F:
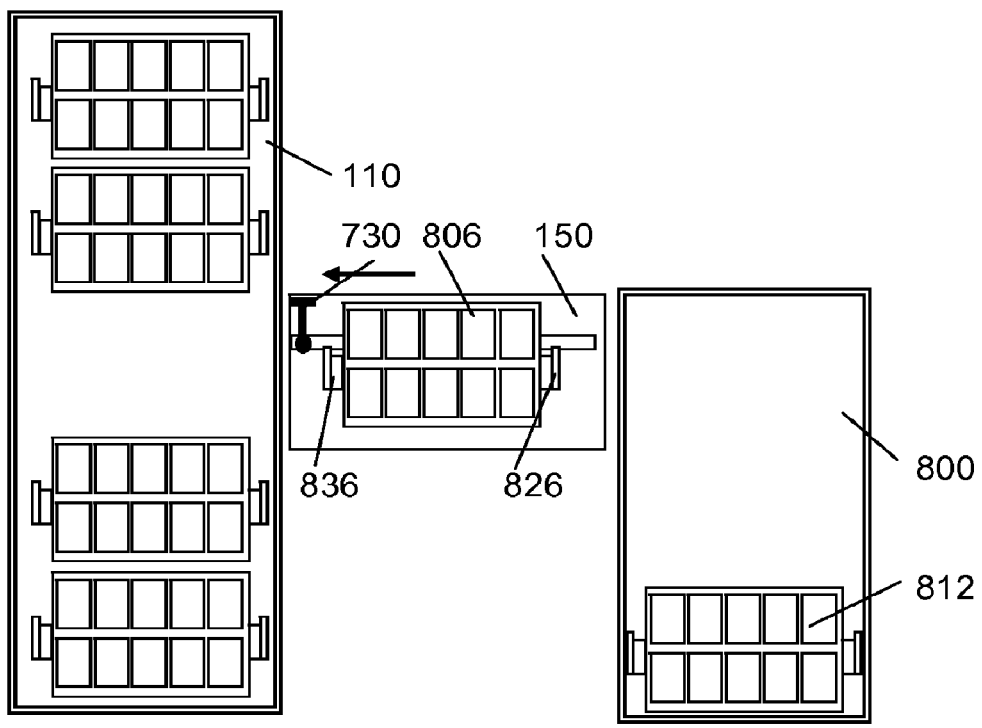
Figure 8G:
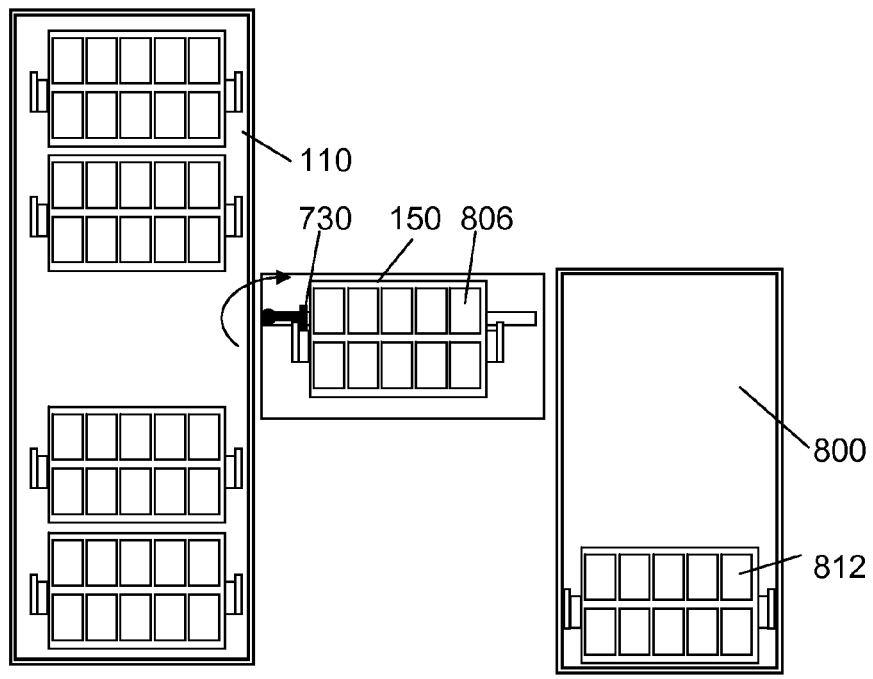
Figure 8H:
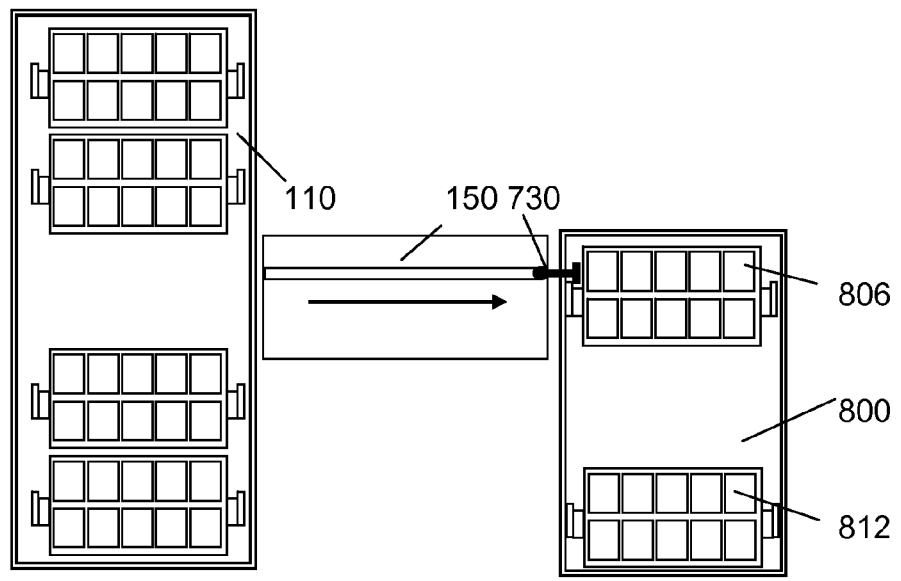
Figure 8I:
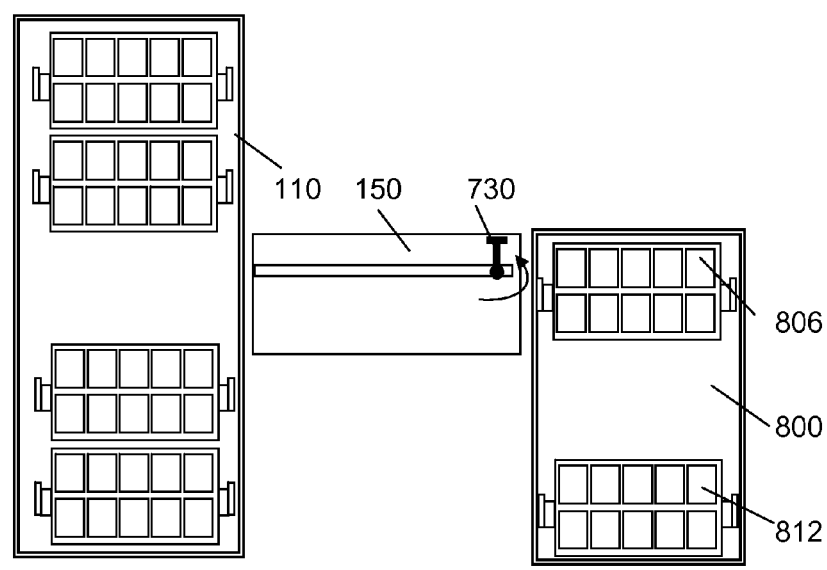
Figure 8J:
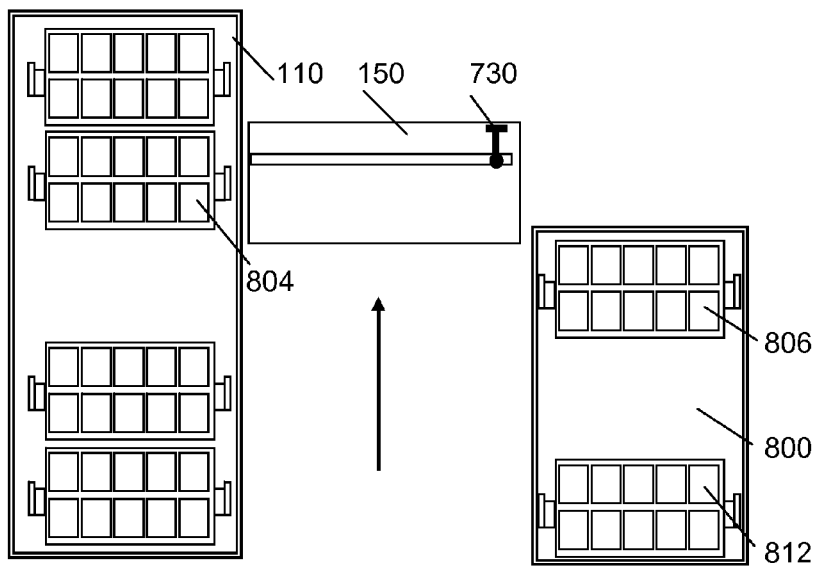
Figure 8K:
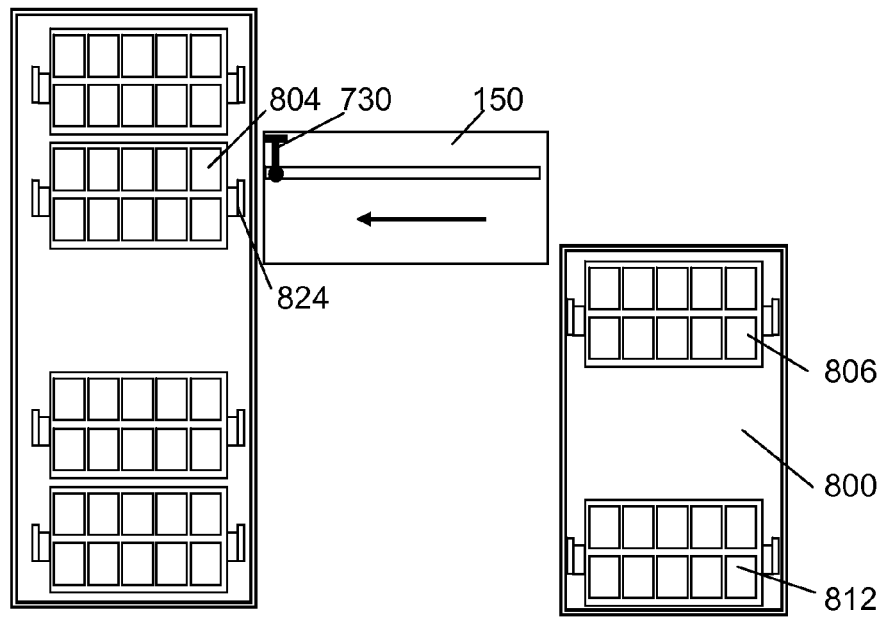
Figure 8L:
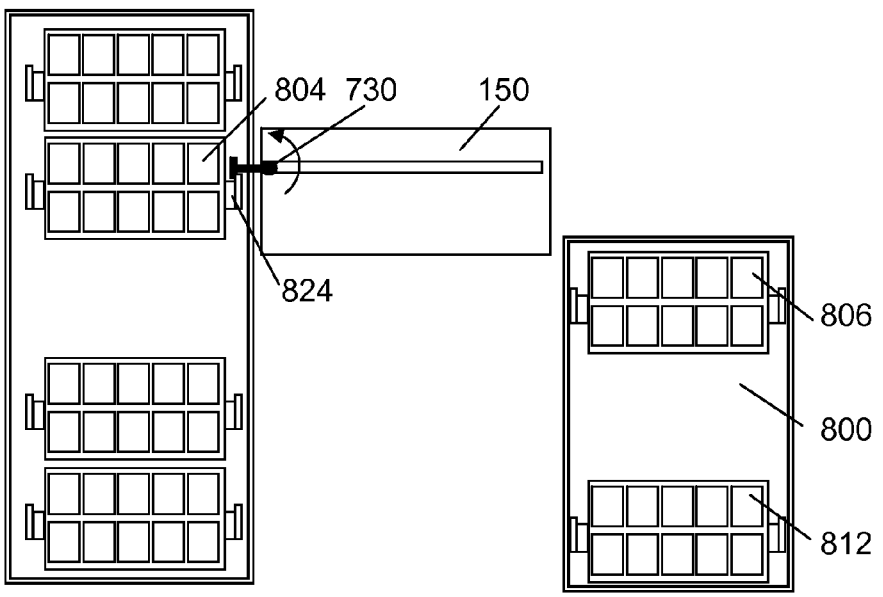
Figure 8M:
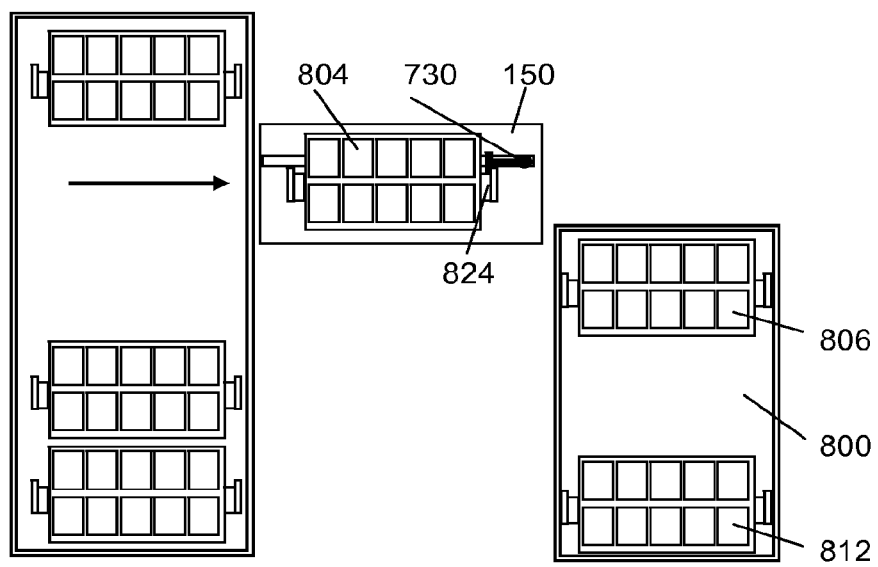
Figure 8N:
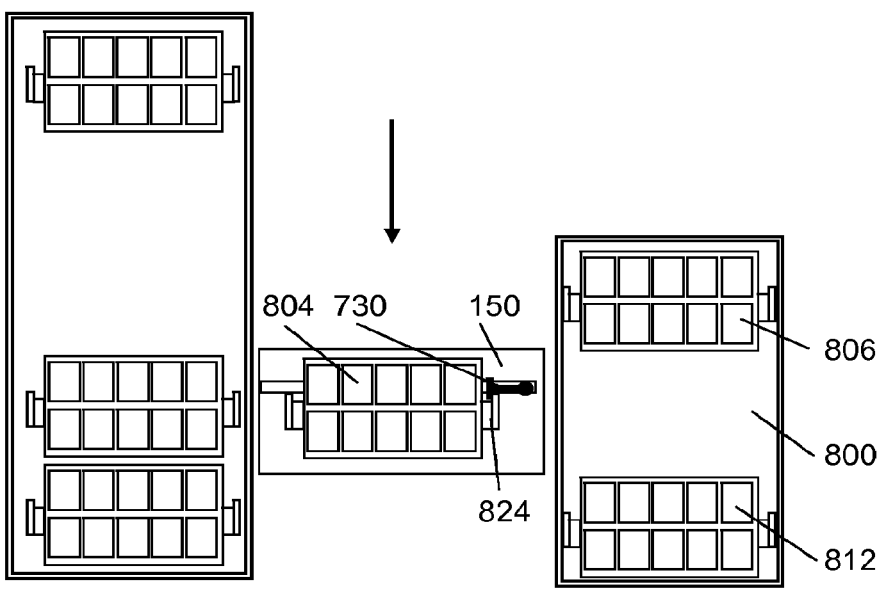

Tray hook motor 732, when activated, rotates tray hook 730 to extend beyond the end of tray shuttle 150 (as shown in FIGS. 8a-8n), so that only hook 730 reaches into the sample storage compartment. Tray hook 730 can be used to either engage tray end hook 720 to enable the tray to be pulled onto tray supports 716, or can push against end hook 720 to slide the tray off of tray supports 716 and away from tray shuttle 150.

FIGS. 8a-8n illustrate a sequence of operations performed by tray shuttle 150 for removing samples from storage compartment 110 and transferring them to module 800. Starting with FIG. 8a, tray 812 is pre-positioned within module 800, which in this example is a cherry picker module. Tray 812 is a receiving tray into which selected samples will be placed during the picking operation. Tray hook 730 is located on the right or front (module), side of tray shuttle 150 when the system controller gives the command to retrieve tray 806, which has been identified as containing samples that are processed. If the storage compartment employs the vertical carousel of the first embodiment, the carousel will be rotated during this step to align tray shuttle 150 with the carrier and tray to be retrieved. The tray shuttle 150 is horizontally aligned with the desired tray 806. For the gantry-mounted tray shuttle of the second embodiment, the gantry will be activated to move the tray shuttle 452 to the appropriate vertical and horizontal position to begin retrieval.

In FIG. 8b, tray hook 730 is moved to the left, or back (storage compartment), side of shuttle 150 by activating drive motor 715 to move slide 714 to the back. In FIG. 8c, tray hook motor 732 is activated to rotate tray hook 730 counterclockwise, causing the end of hook 730 to engage tray end hook 826 of tray 806.

Once the two hooks are engaged, drive motor 715 is activated to move slide 714 toward the front of shuttle 150, pulling tray 806 out of storage compartment 110, as shown in FIG. 8d. If needed at this point, tray shuttle 150 will move laterally along tray shuttle plane 752, or gantry 552 will move tray shuttle 452 horizontally, to position the tray for delivery to module 800. As illustrated, however, module 800 is directly in front of the location from which tray 806 is pulled.

In FIG. 8e, tray hook 830 is rotated clockwise to disengage it from tray end hook 826. Slide 714 is then activated to move it to the back of tray shuttle 150, as shown in FIG. 8f. In FIG. 8g, tray hook 730 is rotated clockwise again to engage end hook 836 of tray 806. Slide 714 is then activated to move to the front of tray shuttle 150, pushing tray 806 through an opening in the back of module 800, as shown in FIG. 8h. Tray hook 730 is rotated counterclockwise to release end hook 836, shown in FIG. 8i, after which tray shuttle 150 moves horizontally along tray shuttle plane 152 to position the shuttle in front of the next tray to be retrieved, in this case tray 804, as shown in FIG. 8j.

During the operation of tray shuttle 150 to complete the steps shown in FIGS. 8g to 8i, in the embodiment of FIGS. 1-3, the vertical carousel can be activated to pre-position the next carrier at the tray shuttle level. Thus, tray 804 need not have been retained within the same carrier as was tray 806. Nonetheless, because of the independent operation of the vertical carousel and the tray shuttle, it is possible to make the next tray available for retrieval immediately after the tray shuttle is freed up after delivery of the previous tray 806 to module 800.

In FIG. 8k, slide 714 is moved toward the back of tray shuttle 150, positioning tray hook 730 in front of tray 804. Tray hook motor 732 is activated to rotate tray hook 730 counterclockwise to engage tray end hook 824, as shown in FIG. 8l. Slide 714 is activated to pull tray 804 onto tray shuttle 150, as shown in FIG. 8m, then tray shuttle 150 is moved along shuttle plane 152 to position tray 804 for transfer to module 800, as shown in FIG. 8n. The steps illustrated in FIGS. 8g and 8h will then be followed to move tray 804 into module 800.

Once the desired samples have been removed from trays 804 and 806, the tray shuttle will operate in a reverse sequence to return the trays to their previous position. Additional trays can be retrieved and transferred to module 800 to obtain all of the desired samples for transfer into tray 812.

After tray 812 is filled with the desired samples, tray shuttle 150 can be used to return the samples to storage or to transfer the tray to a different module. Typically, the second module will perform a processing operation, such as de-frosting the samples in a controlled, e.g., inert and/or temperature ramped, environment to minimize condensation before the samples are removed from the system for use. The same module can be used for introducing samples into the colder temperatures of the storage compartment, subjecting them to an inert atmosphere before they are placed in storage. Other modules can include video or analytical instrumentation for inspection and/or testing of the samples.

FIGS. 9a and 9b illustrate the picker mechanism 902 that is utilized in a cherry picker module 900 for tubes. As previously mentioned, the picker module 900 has two source tray positions 920, 921 and one destination tray position 950, which hold multiple sample racks 922 and 952, respectively. The trays are supported on a stationary surface, or "pick table" 901, while the picker mechanism moves within an x-y plane to access different locations on the trays to perform the desired transfer operations. While samples are being extracted from one source tray position, a different source tray can be moved into the other source tray position, allowing for virtually continuous sample selection.

Picker mechanism 902, which is mounted on a linear translator for movement along one axis 916 (the y-axis in FIG. 9b), includes pick head 904 and pusher mechanism 906. Pick head 904 translates along the other axis (x-axis in FIG. 9b) along rail 910, while the positioning of pusher mechanism 906 is controlled by screw drive 908.

Pusher mechanism 906 lifts the sample containers up and out of the racks 922, pushing them into one or more cavities in pick head 904. The pusher mechanism 906 moves independently from pick head 904, allowing the pick head to receive multiple tubes from different locations of a tray. Once the cavity or cavities in the pick head are full, pick head 904 is moved to a destination over a rack 952 in destination tray 950, where an ejector mechanism is actuated, placing all containers in one motion.

Figure 10A:
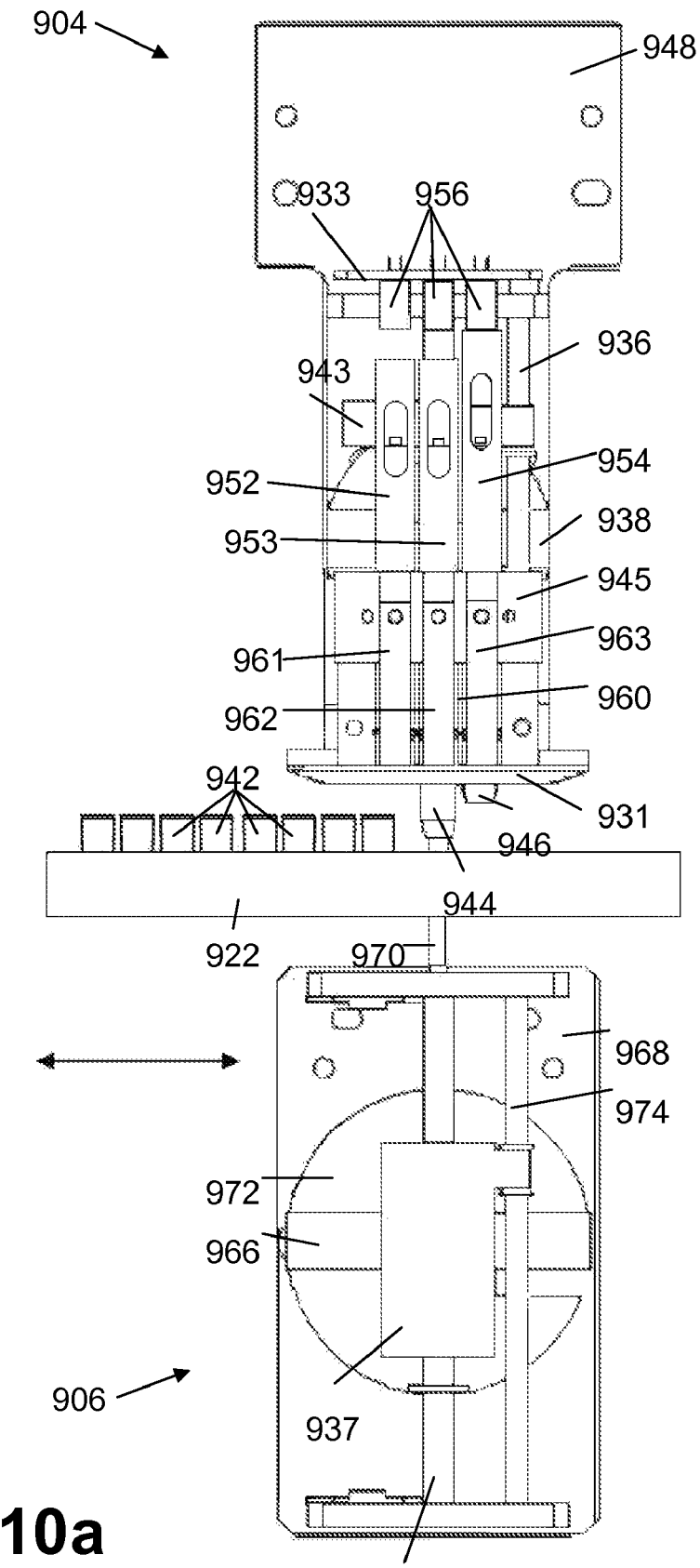
FIGS. 10a-10c are a front, side and perspective views, respectively, of a sample selector mechanism.
Figures 10B, 10D:
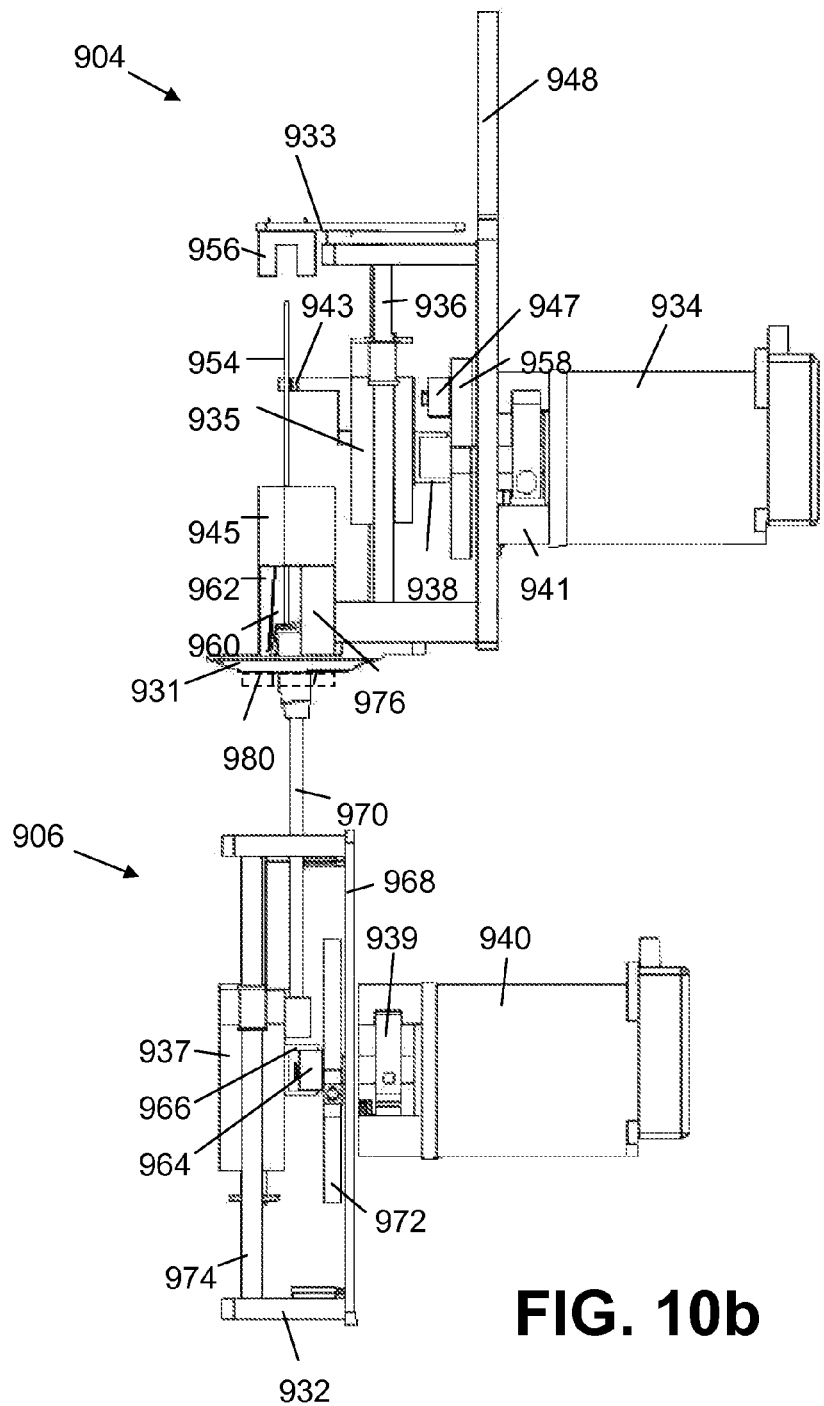
FIG. 10d is a top view of a fixture for use with the sample selector for cutting seals around containers.
Figure 10C:
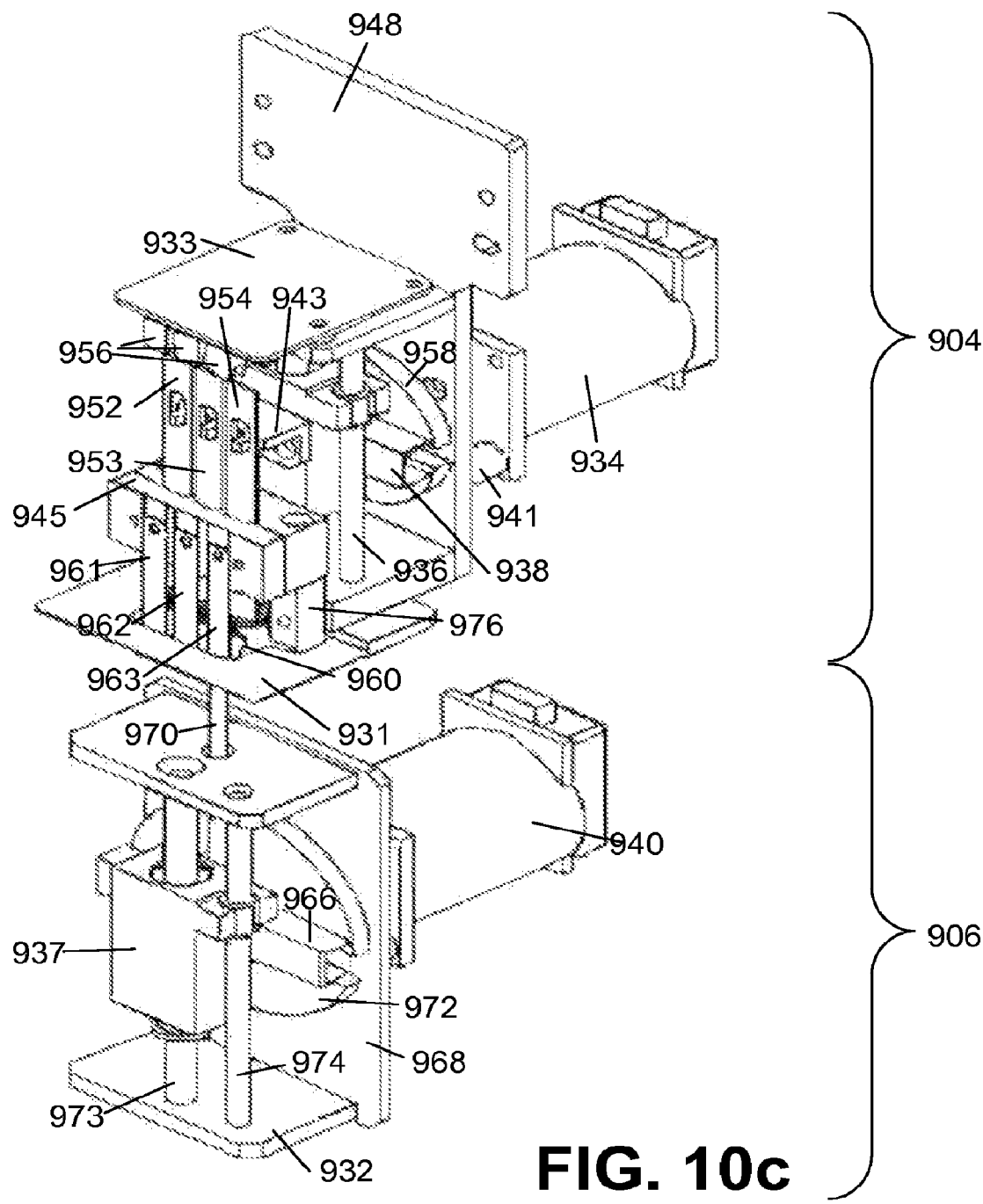

FIGS. 10a-10c illustrate the elements of the pick head 904 and pusher mechanism 906.

Pick head 904 is mounted on rail 910 by way of mounting plate 948, with also provides the frame for attachment of the pick head components. Pick head bottom plate 931 extends perpendicular to mounting plate 948 and has an opening through which the sample containers pass. Bottom plate 931 will generally be located a short distance above the rack 922 from which the samples are being picked. When the picker is also being used to separate tubes that have been sealed with an adhesive sheet, as described below, bottom plate 931 may actually contact the top surface of the rack 922. Just above bottom plate 931 are springs 961-963 which are releasably attached to block 945 to extend downward. Each spring 961-963 is formed from a resilient metal and has an inwardly extending a tapered tooth that causes the spring to cam outward when a sample container is pressed upward against the tooth. The inner surface of each spring 961-963, the lower surface of block 945, and back wall 976 define cavity 960 within which sample containers can be retained during the picking process. The size of the cavity, which is primarily defined by the length of springs 961-963 between the upper edge of the tapered tooth and the bottom surface of block 945, should closely fit the size of the container in order to ensure proper operation. When different length containers are to be handled, the springs 961-963 are removed by unscrewing the spring screws and replaced with springs that have lengths corresponding to the containers to be handled. The spring retains its associated container within cavity 960 until the container is ejected.

Sensor/ejector blades 952-954 slidably extend through slots in block 945 so that when a container is pushed into cavity 960, the blade above the container is pushed upward so that the upper end of the blade is positioned for detection by one of a set of optical detectors 956 that are mounted on a printed circuit board 933 above block 945. (PCB 933 provided electrical connection to the picker controller (not shown).) Activation of the optical sensor 956 produces a signal that tells the picker controller that a container is retained within a given slot in the pick head. As illustrated in FIG. 10 a, container 946 is retained within cavity 960, thus pushing blade 954 upward where its upper end is detected by optical sensor 956. Container 944 is in the process of being pushed up against the tapered tooth of spring 962 by pusher rod 970. The top of container 944 will contact with the lower edge of blade 953 to push it upward where it, too, will be detected by the corresponding optical sensor 956. In the exemplary embodiment, the pick head is configured for accepting three containers, as there are three springs 961-963, three blades 952-954 and three optical sensors 956. Once all optical sensors have detected the presence of a container in the cavity 960, the picker controller directs the pick head to move to a position of a destination rack 950 (in FIG. 9b) into which the sample containers are to be placed. Once the pick head is in position over destination rack 950, cam motor 934 is activated to rotate flywheel 958, causing cam wheel 947 to apply a downward force against channel 938. Channel 938 is attached to the back side of pick head slide 935, causing slide 935 to move downward along guide 936. Extending from the front side of slide 935 is ejector bar 943, which has an ejector tab that extends through a slot in each of blades 952-954. As slide 935 moves downward, ejector bar forces blades 952-954 downward against the tops of the containers in cavity 960, ejecting them simultaneously from the pick head and into the destination rack. Flywheel 958 can be weighted to provide additional inertia upon activation to ensure that it follows its full cycle.

While the above explanation describes a pick head adapted for receiving three containers, it will be readily apparent that more or fewer containers can be handled by providing from one cavity-spring-blade-sensor combination to many such combinations as may be practical for efficient operation.

Pusher mechanism 906 cooperates with pick head 904 by driving pusher rod 970 upward, through the open bottoms of tray 920 and rack 922 to lift one of containers 942 up and push it upward against the toothed springs of the pick head. Pusher mechanism 906 is attached to translator 908 via mounting plate 968 to permit independent movement of the pusher and pick head. Pusher rod is attached to pusher slide 937 which moves vertically along column 973, stabilized by pusher guide 974, both attached to base 932. Vertical motion is initiated by a similar cam mechanism as that described above for the pick head ejector. Cam motor 940 rotates flywheel 972, which moves cam wheel 964 within channel 966 to apply upward or downward force against the channel 966. Channel 966, which is attached to the back side of pusher slide 937, causes pusher rod 970 to move up or down, depending on the direction of rotation of flywheel 972. As with the pick head, flywheel 972 can be weighted to ensure that it produces sufficient inertia to complete its full cycle. Pusher rod 970 can be replaced with different length rods as may be needed for handling different length containers.

Each of cam motor assemblies 934, 940 includes a magnetic position sensor 941 or 939, respectively, which provides feedback on the position of the corresponding flywheel 958 or 972 to ensure that the flywheel is rotated through its full cycle. Control electronics are located within the boxes attached to the ends of the motors.

Pick head 904 can be modified to perform the function of die cutting, thus eliminating the need for an additional step, and additional instrumentation, for separating containers within a rack that have been sealed with a single sheet of foil or polymer. In this embodiment, a cutting plate 980 is affixed to the bottom of pick head bottom plate 931 with cutting edge 982 aligned with the bottom of cavity 960. Cutting plate 980 can be formed from aluminum or stainless steel. Edge 982 need not be intentionally sharpened since the normal process of machining the plate to form the opening by cutting or drilling produces a sharp enough edge to cut the seal around the perimeter of the sample container when it is pushed upward by the pusher mechanism. This allows the tubes to be stored with the seal intact until needed. Typically only a few samples are needed at a time, so the seal is cut only around the containers of the samples that are desired when they are prepared for selection.

Figure 12:
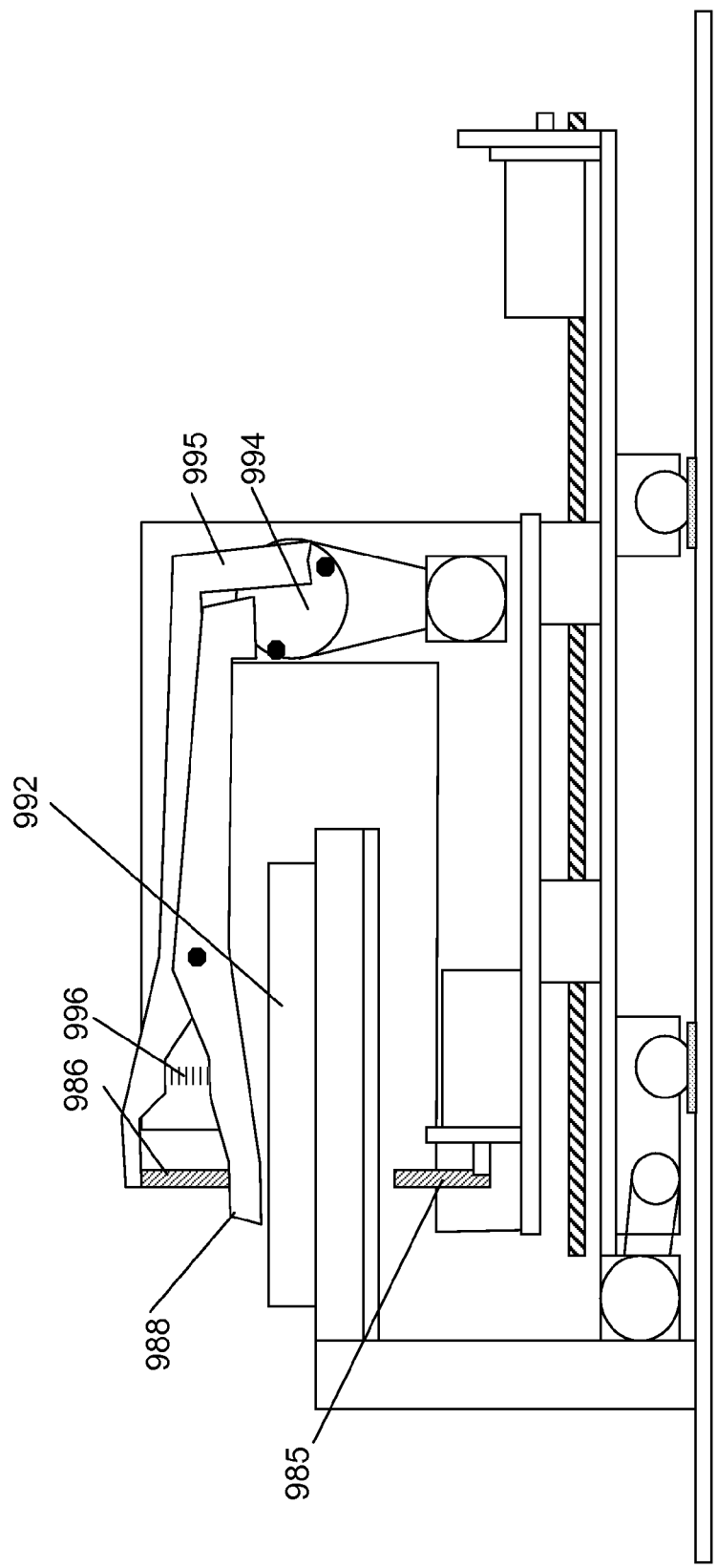
FIG. 12 is a diagrammatic view of an alternative embodiment of a sample selector.

FIG. 12 illustrates an alternative embodiment of the cherry picker where the pick head carries a single sample at a time. In this case, the pick head 988 and pusher 985 are supported on the same frame and do not move independently of each other. This configuration is particularly suited for handling racks 992 that hold very small (50-100 microliter) tubes, which are the type most commonly sealed with a sheet 990 of foil or polymer. Such racks may hold as many as 384 tubes. Since the ejector in the pick head is only required to release one tube at a time, the ejector mechanism is a single pin 986 that is activated by a cam 994 that lifts up on lever 995 to compress bias spring 996 to apply downward force against a tube within the pick head cavity.

Figure 13B:
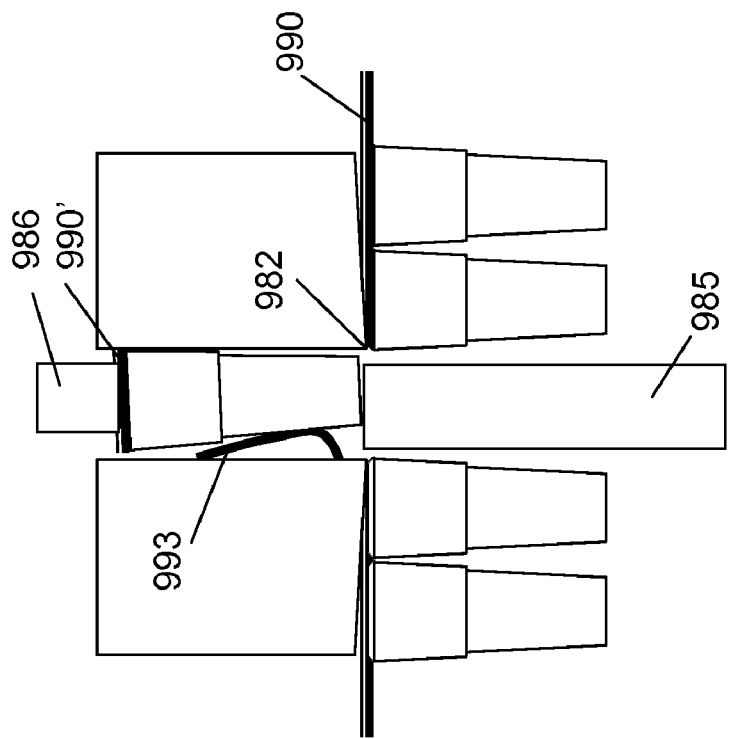
FIGS. 13a and 13b are diagrammatic views of the sample selector of FIG. 12 before and after die cutting of a sealing sheet.
Figure 13A:
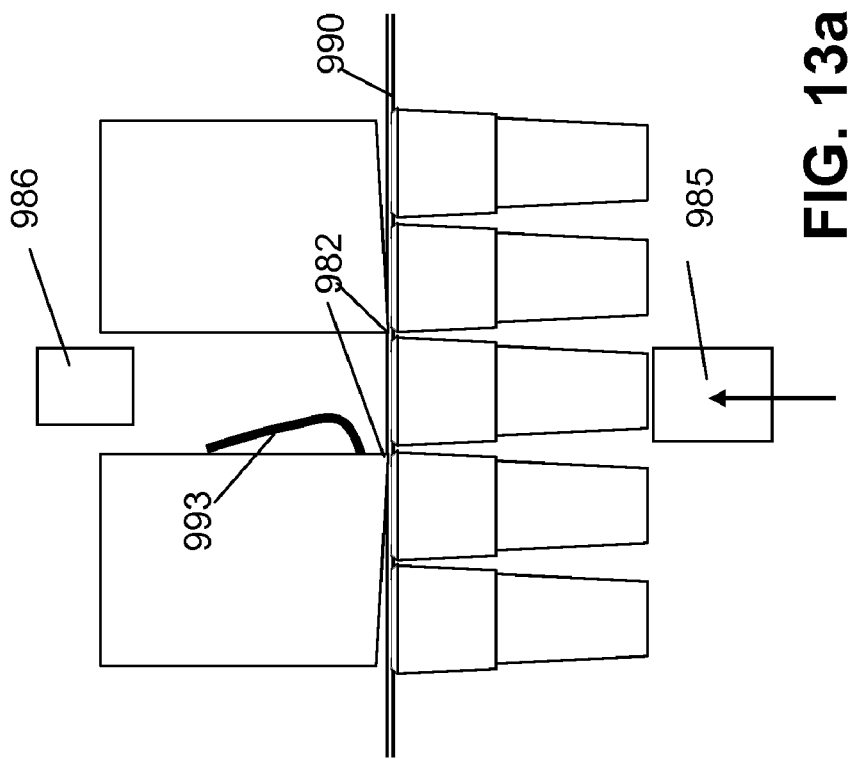

As illustrated in FIGS. 13a and 13b, the cherry picker mechanism of FIG. 12 is particularly well adapted for separating tubes that have been sealed with a sheet 990. When pusher 985 applies force against the bottom of the tube, it is pressed against the sharp edges 982 of the pick head, cutting the seal 990' to separate the tube which is then pushed up into the cavity, in contact with spring 993 and ejector pin 986. When the cherry picker is moved to the destination tray, ejector pin is activated to press downward on the tube to push it out of the cavity.

The sample storage systems described herein address many of the shortcomings of prior art systems to provide rapid access to samples in an environmentally controlled storage compartment with minimal impact on the storage compartment environment. The flexible modules that can be interchangeably and separably attached to the storage compartment are capable of continuous operation when used in conjunction with a robotic tray shuttle mechanism with a minimum number of electromechanical components that can be negatively impacted by the low temperature storage environment.

The cherry picker mechanism provides for rapid retrieval of selected samples without subjecting other samples in the same tray to environmental changes. Multiple cherry picker modules can be associated with a single storage compartment and tray shuttle so that different types and sizes of sample containers can be stored, handled and managed within the same storage system.

It will be apparent to those skilled in the art that various modifications and variations may be made in the system and devices of the present invention without departing from the spirit and scope of the invention. Thus, it is intended that the present invention encompass all such modifications and variations to the extent that they fall within the scope of the appended claims and their equivalents.

The invention claimed is:

1. A device for retrieving or replacing individually identified sample vials retained in a tray within a storage compartment, the storage compartment having a plurality of storage positions at horizontal and vertical locations within the compartment, the device comprising:

a controller for generating commands to retrieve one or more vials of interest from a corresponding storage position in the storage compartment, and to replace one or more vials of interest to the storage compartment;

a tray shuttle having a storage side adjacent the storage compartment and a load/unload side, wherein the tray shuttle is responsive to commands from the controller, the tray shuttle comprising:

a tray shuttle frame extending along a width of the storage compartment;

a tray support;

a tray shuttle slide disposed on the tray shuttle frame for horizontal translation of the tray support across the width of the storage compartment, wherein, in response to a retrieve command to retrieve one or more vials of interest, the tray shuttle slide moves the tray support along the width of the storage compartment to a pre-determined storage location corresponding to a storage tray that contains the one or more vials of interest;

a tray hook slidably disposed on the tray shuttle slide to traverse a length of the tray support between the storage side and the load/unload side, wherein, in response to the retrieve command, the tray hook rotates to extend from the tray support to engage a first tray end hook of the storage tray containing the one or more vials of interest and slides toward the load/unload side so that the storage tray is pulled away from the storage compartment, toward the load/unload side and onto a surface of the tray support;

a vial selector module disposed at the load/unload side, comprising:

a pick table disposed in an x-y plane for receiving and supporting the storage tray that contains the one or more vials of interest and a destination tray, wherein each of the storage tray and the destination tray have an open bottom through which vials are accessed;

a pusher disposed below one of the storage tray and the destination tray, the pusher comprising a push rod adapted for raising and lowering the push rod through the open bottom in the one of the storage tray and the destination tray;

a pick head disposed above the one of the storage tray and the destination tray, the pick head having at least one cavity for releasably retaining a vial of interest;

one or more translators for translating the pick head and the pusher within the x-y plane to access the one or more vials of interest in the storage tray and all positions in the destination tray, wherein:

if the one or more vials of interest are to be removed from the storage tray, the pick head and pusher are translated within the x-y plane until they are aligned with a position in the storage tray at which the one or more vials of interest are located and the push rod is raised to lift the one or more vials of interest from the storage tray by pushing upward through the open bottom of the storage tray until the one or more vials are supported within the at least one cavity, and if the one or more vials of interest are to be inserted into the destination tray, the pick head and pusher are aligned with a destination position in the destination tray and the push rod is raised through the open bottom of the destination tray then lowered to lower the vial of interest from the cavity into the destination tray;

wherein the controller further generates commands to the tray shuttle to retrieve the storage tray after removal of the one or more vials of interest and return the storage tray to the pre-determined storage position, and to retrieve additional storage trays to select additional vials of interest to transfer the additional vials of interest to the destination tray; and an access door for removing the destination tray from the vial selector module.

2. The device of claim 1, wherein the tray hook is further operable, in response to an unload command, to rotate to disengage the first tray end hook, slide toward the storage side of the tray support, to rotate to engage a second tray end hook, to slide toward the load/unload side to push the storage tray away from the tray support and onto the unload location, and to rotate to disengage the second tray end hook to release the storage tray.

3. The device of claim 1, wherein the tray shuttle slide comprises a gantry for further providing vertical motion.

4. The device of claim 1, wherein the tray shuttle is enclosed within a temperature controlled compartment.

5. The device of claim 1, wherein the vial selector module comprises an environmentally controlled enclosure.

6. The device of claim 1, wherein the vial selector module further comprises a tracking device for detecting the identities of the one or more vials of interest and providing the detected identities to the controller.

7. A device for retrieving or replacing individually identified sample vials retained in a storage tray within a storage compartment, the storage compartment having a plurality of storage positions at horizontal and vertical locations within the compartment, the device comprising:

a tray shuttle comprising:

a tray shuttle compartment, the tray shuttle compartment having a storage side adjacent the storage compartment and a load/unload side;

a tray shuttle frame extending along a width of the tray shuttle compartment;

a tray shuttle comprising a tray support and a tray shuttle slide disposed on the tray shuttle frame for horizontal translation of the tray support across the tray shuttle frame to a pre-determined location of the storage tray containing a vial of interest;

a tray hook slidably disposed on the tray shuttle slide;

a tray hook motor disposed on the tray shuttle slide for rotating the tray hook clockwise or counterclockwise to engage or disengage a tray end hook of the storage tray;

a drive assembly for sliding the tray hook and tray hook motor across a length of the tray support between the storage side and the load/unload side, wherein, when the tray hook is engaged with a first tray end hook, the drive assembly pulls the storage tray onto the tray support, and when the tray hook is engaged with a second tray end hook, the drive assembly pushes the storage tray away from the tray support; and a vial selector module disposed at the load/unload side of the tray shuttle compartment, the vial selector module comprising:

a pick table disposed in an x-y plane for receiving and supporting the storage tray and a destination tray, wherein each of the storage tray and the destination tray have an open bottom;

a pusher translatable within the x-y plane so that it is disposed below a plurality of vial-retention positions of one of the storage tray and the destination tray, the pusher comprising a vertically-movable push rod for raising and lowering the push rod through the open bottom in one of the storage tray and the destination tray;

a pick head translatable within the x-y plane so that it is disposed above the plurality of vial-retention positions of one of the storage tray and the destination tray, the pick head having at least one cavity for releasably retaining the vial of interest;

wherein, for removal of the one or more vials of interest from the storage tray, the pick head and pusher are translated within the x-y plane until they are both aligned with the vial-retention position in the storage tray at which the vial of interest is located and the push rod is raised to lift the vial of interest from the storage tray by pushing upward until the vial of interest is supported within the at least one cavity, after which the push rod is lowered, and for insertion of the vial of interest into the destination tray, the pick head and pusher are aligned with a destination position in the destination tray and the push rod is raised then lowered to lower the vial of interest from the cavity into destination position of the destination tray.

8. The device of claim 7, wherein the tray shuttle slide comprises a gantry for further providing vertical motion.

9. The device of claim 7, wherein the tray shuttle is enclosed within a temperature controlled compartment.

10. The device of claim 7, wherein the vial selector module comprises an environmentally controlled enclosure.

11. The device of claim 7, wherein the vial selector module further comprises a tracking device for detecting the identities of the one or more vials of interest and providing the detected identities to a system controller.

* * * * *